US007939679B2

(12) United States Patent
Hirama et al.

(10) Patent No.: US 7,939,679 B2
(45) Date of Patent: May 10, 2011

(54) METHOD FOR SYNTHESIS OF CIGUATOXIN CTX1B AND COMPOUNDS USEFUL FOR THE SYNTHESIS OF CIGUATOXIN CTX1B

(75) Inventors: Masahiro Hirama, Miyagi (JP); Masayuki Inoue, Tokyo (JP)

(73) Assignee: Japan Science & Technology Agency, Saitama (JP)

( * ) Notice: Subject to any disclaimer, the term of this patent is extended or adjusted under 35 U.S.C. 154(b) by 210 days.

(21) Appl. No.: 12/161,047

(22) PCT Filed: Jan. 10, 2007

(86) PCT No.: PCT/JP2007/050545
§ 371 (c)(1),
(2), (4) Date: Jul. 16, 2008

(87) PCT Pub. No.: WO2007/083638
PCT Pub. Date: Jul. 26, 2007

(65) Prior Publication Data
US 2010/0160651 A1     Jun. 24, 2010

(30) Foreign Application Priority Data

Jan. 19, 2006   (JP) ................................ 2006-011297

(51) Int. Cl.
*C07D 313/00* (2006.01)
(52) U.S. Cl. ...................................................... 549/354
(58) Field of Classification Search .................... 549/354
See application file for complete search history.

(56) References Cited

OTHER PUBLICATIONS

"A concise route to the right wing of ciguatoxin", Tatami et al., Tetrahedron Letters 44 (2003), p. 5229-5233.

"Synthesis of the Fully Functionalized ABCDE Ring Moiety of Ciguatoxin", Kobayashi et al., Organic Letters, 2004, vol. 6, No. 5, p. 751-754.
"Total Synthesis of Ciguatoxin and 51-HydroxyCTX3C", Inoue et al., J. Am. Chem. Soc. 2005, 128, p. 9352-9354.
"First- and second-generation total synthesis of ciguatoxin CTX3C", Inoue et al., PNAS, Aug. 17, 2004, vol. 101, No. 33, p. 12013-12018.
"Synthesis-Based Approach toward Direct Sandwich Immunoassay for Ciguatoxin CTX3C", Oguri et al., J. Am. Chem. Soc., 2003, 125, p. 7608-7612.
"A New Stereoselective Synthesis of Ciguatoxin Right Wing Fragments", Inoue et al., J. Org. Chem. 2004, 69, p. 2797-2804.
Supplemental European Search Report (SESR) for corresponding Application No. EP 07706872.4-2101/1982988, PCT/JP2007050545 (Mar. 11, 2010).
M. Hirama et al.: "Total Synthesis of Ciguatoxin CTX3C," Science, vol. 294, pp. 1904-1907, 2001 (Washington, DC, USA), XP002572475, Figures 1-3 (Cited in SESR).

*Primary Examiner* — Nizal S Chandrakumar
(74) *Attorney, Agent, or Firm* — Hahn & Voight PLLC; Roger C. Hahn

(57) ABSTRACT

Disclosed is a method for total synthesis of CTX1B, which is developed for the synthesis of a ciguatoxin analogue such as CTX3C and enables the more efficient application of an established reaction to the total synthesis of CTC1B. More specifically, disclosed is a method for total synthesis of CTX1B comprising; an O.S-acetal formation for synthesizing a novel compound (3); a radical cyclization reaction for constructing a 9-membered ring formation reaction including a novel compound (6) through a novel compound (8) and yielding a compound (D); and a deprotection for yielding CTX1B. Also disclosed are novel compounds (1) to (8) which are particularly useful for synthesis of CTX1B and can be used for the synthesis of a ciguatoxin analogue.

9 Claims, No Drawings

METHOD FOR SYNTHESIS OF CIGUATOXIN CTX1B AND COMPOUNDS USEFUL FOR THE SYNTHESIS OF CIGUATOXIN CTX1B

FIELD OF THE INVENTION

The present invention relates to the establishment of a method for total synthesis of ciguatoxin CTX1B which is a homolog of ciguatoxin, further, relates to a provision of compounds useful to make possible an effective method for preparation of said total synthesis.

BACKGROUND OF THE INVENTION

Food-poisoning, ciguatera caused by poisoning of originally non-toxic fishes, widely occurs in coral reef islands region of subtropical and tropical regions, and more than 50,000 people suffer annually from ciguatera. Although the mortality is not so high, symptoms such as abnormal sensation, diarrhea, lassitude, arthralgia or itching last for several months under some circumstances. Ciguatoxins (CTX), which are isolated and the structure of which is decided as a main originated poison of ciguatera, are macromolecules characterized by fused 13 ether rings and their molecular length is approximately 3 nm, further more than 20 kinds of homolog are existing. Ciguatoxins are produced from dinoflagellate *Gambierdiscus toxicus* and accumulate in fishes by means of food chain. Since approximately 400 kinds of toxic fishes are normal from the view points of appearance, taste and odor, it is not safe to exploit fish sources of southern sea region. Therefore, the development of detective method of ciguatoxins by means of easy and high sensitive immunological measuring method of ciguatoxins is strongly expected.

Ciguatoxins bind specifically to voltage-sensitive $Na^+$ channels (VSSC) of excitable membranes, activate it and generate toxicity, however, the activation mechanism of ciguatoxins at structural level is not made clear yet. Ciguatoxins exist in nature is very small and cultural production by the dinoflagellate is very slow, detail biological research and the preparation of anti-CTX antibody using natural product is virtually impossible. Under said circumstances, the quantitative supply of natural ciguatoxins by practical chemical synthesis is strongly desired.

Inventors of the present invention already proposed a total synthesis of CTX3C, which is one of main homolog of ciguatoxin (non patent document 1, Proc. Natl. Acad. Sci. U.S.A. 101, 1203-12018 (2004)). Further, the inventors developed a Sandwich immunoassay that can detect CTX3C easily (non patent document 2, J. Am. Chem. Soc. 125, 7608-7612 (2003)) and are now investigating to apply it to identification of a ciguatera fish. However, since CTX3C is mainly contained in a herbivorous fish, preparation of an antibody originated to other homolog is necessary for detection of ciguatoxin from a carnivorous fish.

CTX1B is the most typical ciguatoxin contained mainly in a carnivorous fish and has more complicated structure than CTX3C, and is known as the most historically important ciguatoxin whose structure is firstly decided in 1989. At the decision of structure, 0.3 mg of CTX3B isolated from 4000 kg of poisonous moray is used. However, since it was actually impossible to obtain practical amount of sample from nature, development of total synthesis of CTX1B is awaited for the actual use of CTX1B as a standard sample.

Generally, in total synthesis, if partial structure is different, development of a new synthesis route becomes necessary. However, for the purpose to synthesis many ciguatoxin homologs existing in nature in a unified fashion, the inventors have developed convergent total synthesis, which is characterized to be remarkably simple and more reliable compared with competitive methods. By said method, supply of over than several mg of CTX3C became possible up to this time. According to said concept, since there is possibility that carnivorous fishes accumulate ciguatoxin by higher concentration than herbivorous fishes because carnivorous fishes are locating at upper position of food chain than herbivorous fishes and is more dangerous as a ciguatera poisoned fish, the inventors of the present invention considered to develop a new effective total synthesis of CTX1B for the purpose of investigation of CTX1B.

At the development of a new effective total synthesis, the inventors of the present invention considered to utilize the reaction sequence which were already developed for synthesis of CTX3C. Namely, the inventors considered to apply the coupling of ABCDE ring segments with HIJKLM ring segments and subsequent construction of FG ring to CTX1B. However, since 7-members ring E-structure, and a side chain existing in A ring segments of CTX1B are structurally different from CTX3C, direct application of methodology used in CTX3C was impossible. Therefore, the inventors planned to develop a higher yielding process from a view point of effective preparation of the aimed compound.

(1) At the formation of 7-members ring of compound D at radical ring forming reaction, preparation process of CTX3C can not be used. Therefore, the inventors designed compound 5 that has pentafluoroacrylate instead of conventionally used methylacrylate and yield of ring forming reaction is remarkably improved.

(2) At deprotection of naphthylmethyl (NAP) group, side chain of A ring segment is very unstable to acid and compound E acetal intermediate is formed at conventional acid hydrolysis of acetal. Therefore, various investigations for condition are carried out and it is understood that acetal can be removed by condition of 1N hydrochloric acid/methanol, and the total synthesis of CTX1B can be carried out for the first time. Further, at above mentioned development, the inventors considered to utilize HIJKLM ring segments compound A, which was already reported in a paper (non-patent document 3, J. Org. Chem. 69, 2797-2804 (2004)), and compound C (non-patent document 4, J. Org. Lett., 6, 751-754 (2004)) as one of intermediates, according to the thinking that O,S-acetal compound 3, which is the most important intermediate, can be synthesized by coupling reaction developed by the inventors that permits neutral condition.

SUBJECT OF THE INVENTION

The subject of the present invention is to provide an effective method for total synthesis of CTX1B by high yield. Aiming to accomplish said subject, the inventors of the present invention considered that the designing of an intermediate that can apply an established reaction to be considered rational in synthesis of ciguatoxin analogous compound is important. That is, the subject of this invention is to provide an useful compound that can be used for an effective method for total synthesis of CTX1B, further to link to an improvement of synthesis of ciguatoxin analogous compound.

From said points of view, the inventors of the present invention continued investigation and adopted O,S-acetal forming reaction that synthesizes compound 3, and 9-rings forming reaction from compound 6-8, further, developed a radical ring-forming reaction to obtain aforementioned compound D and a deprotection reaction to obtain CTX1B newly, and by synthesizing all new compounds to link the intermediate to aimed compound, and can accomplish the aforementioned subject.

DISCLOSURE OF THE INVENTION

The first one of the present invention is a method for synthesizing the aimed compound of CTX1B including following 10 processes. First process is comprised of oxidizing double bond in compound A by using osmium tetra oxide to change to a diol derivative of compound A, and after transforming the diol to an aldehyde by oxidation cleavage by using sodium periodate, reducing the aldehyde to alcohol using sodium borohydride to obtain compound 1 (process 1).

compound A 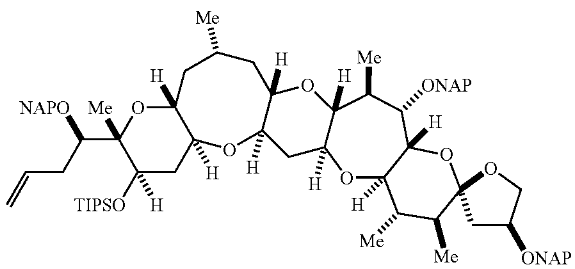 compound 1

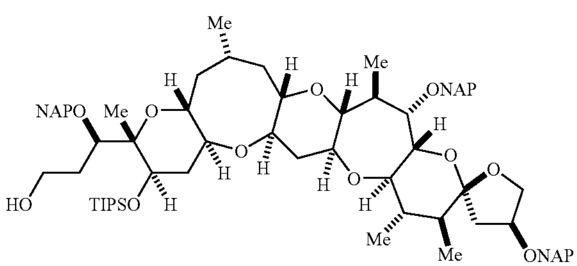

Second process is transforming the alcohol of compound 1 to compound 2 using diphenyldisulfide•tributylphosphine (process 2).

compound 2

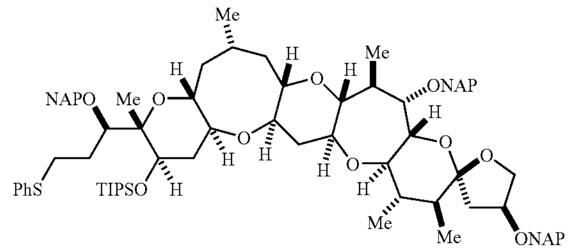

Third process comprises of transforming the compound 2 toα-chrolosulphide to synthesize the compound B, and synthesizing compound 3 by joining the ABCDE ring segments compound C (Refer to the non-patent document 4, J. Org. Lett., 6, 751-754 (2004)) and the compound B as O,S-acetal using silver triflate (AgOTf) (process 3), under the presence of DTBMP (2,6-di-t-butyl-4-methylpyridine).

compound B 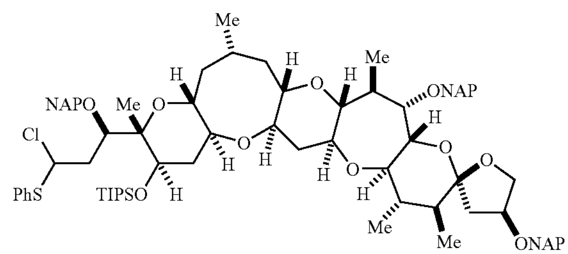 (process 3).

compound 3

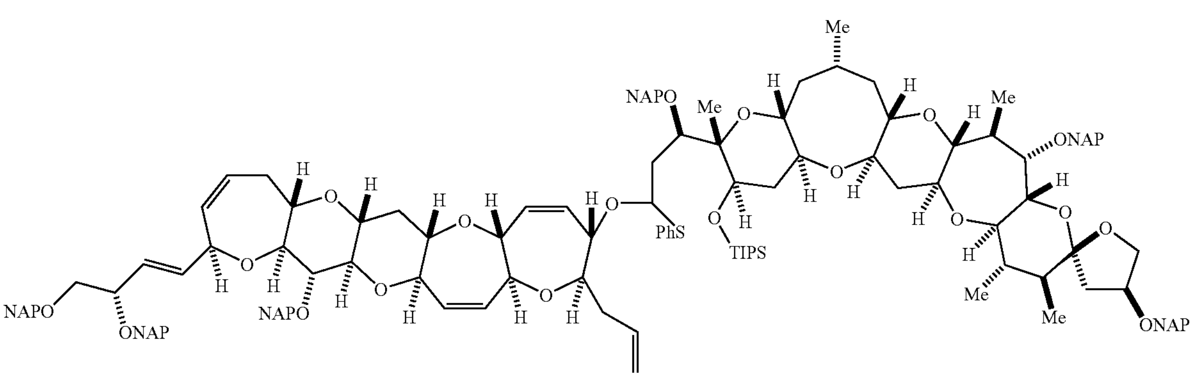

Forth process is forming the compound 4 by removing TIPS (triisopropylsilyl) group from the compound 3 using TBAF (tetrabutylammonium fluoride) (process 4).

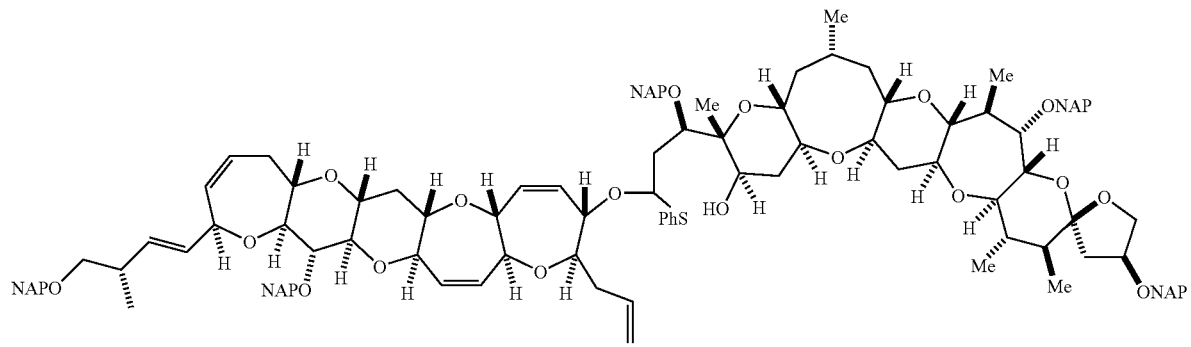

compound 4

Fifth process is forming the compound 5 by joining pentafluorophenylpropiolate to alcohol of above mentioned compound 4 (process 5).

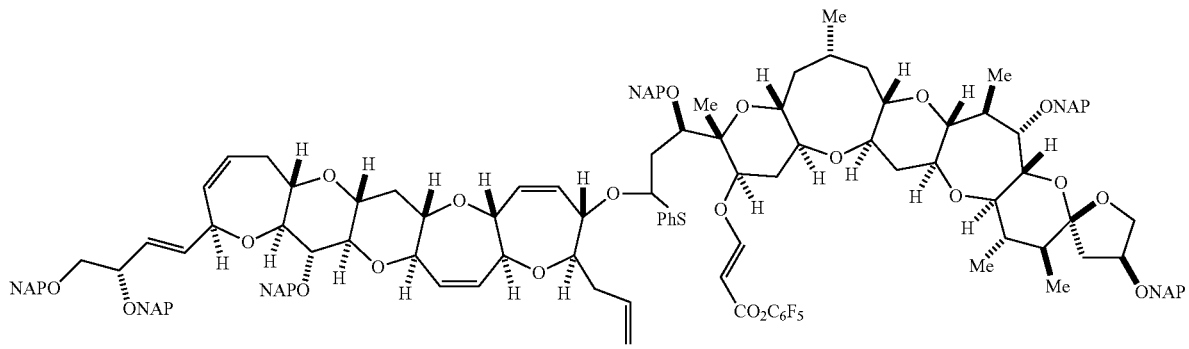

compound 5

Sixth process comprises of transforming the compound 5 to carboxylic acid compound D by forming G ring part by carrying out radical cyclizing reaction on said compound 5 treating by AIBN ($\alpha,\alpha'$-azobis(isobutyronitrile)) and tributyltin hydride, and

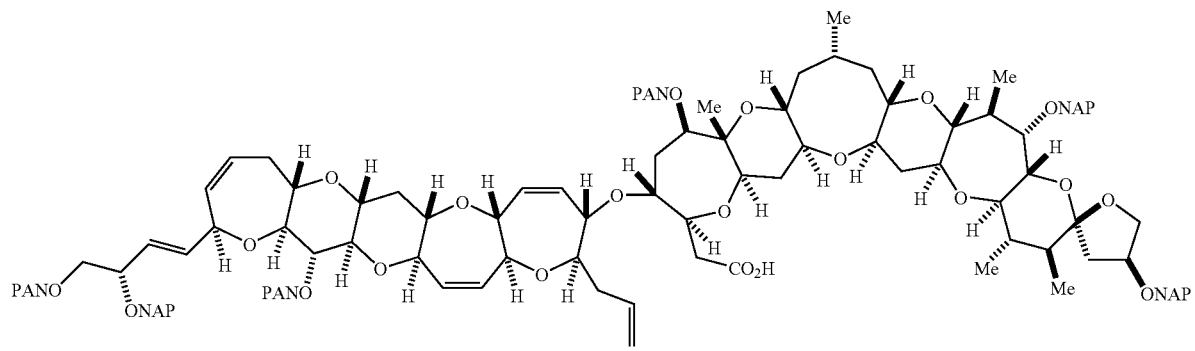

compound D transforming to methyl ester by acting trimethylsilyldiazomethane and to form compound 6 (process 6).

compound 6

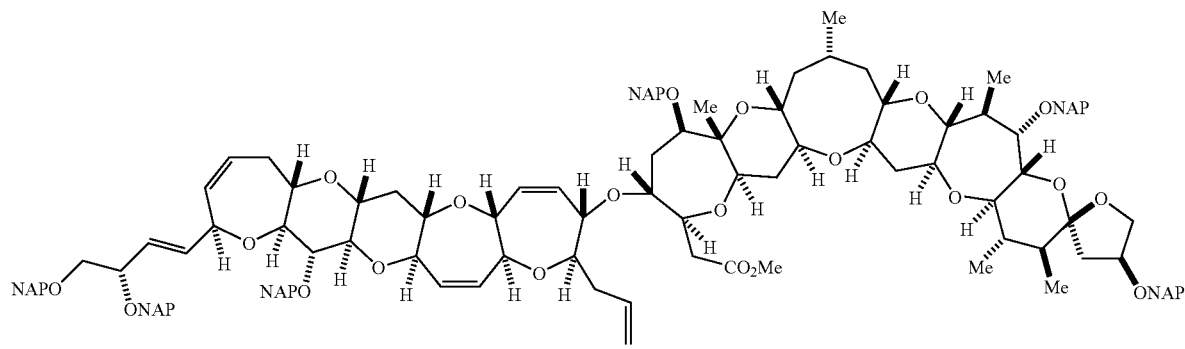

Seventh process is forming compound 7 by reducing methyl ester of above mentioned compound 6 by using diisobutylaluminum hydrate under lower temperature condition, then transforms to olefin by Wittig reaction (process 7).

compound 7

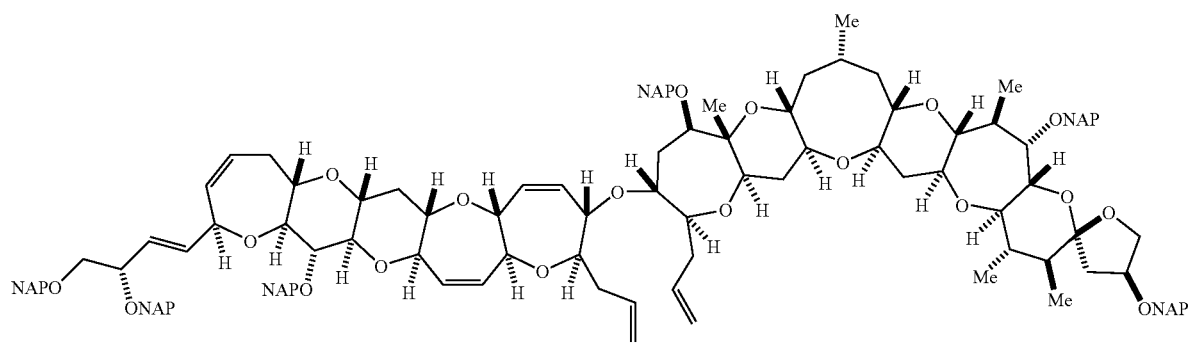

Eighth process is forming compound 8 by forming F ring part by carrying out ring closure methathesis reaction acting Grubbs catalyst to above mentioned compound 7 (process 8).

compound 8

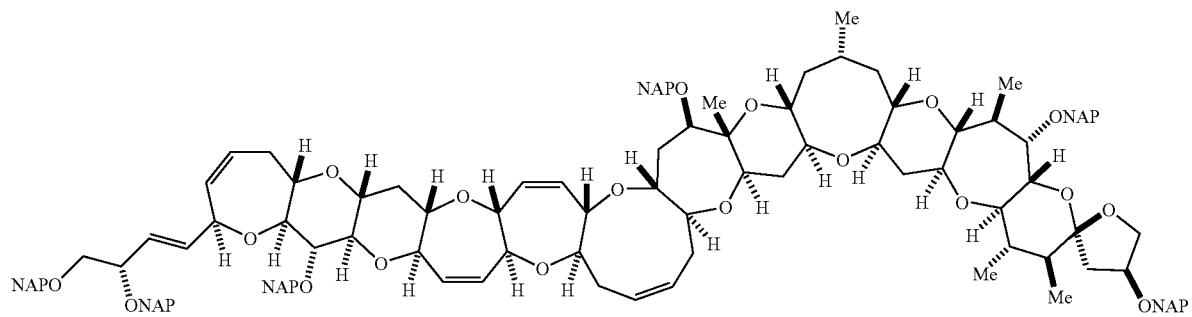

Ninth process is synthesizing compound E, 1,2-diol of A ring side chain of which is protected by naphthylacetal, by oxidizing 6 NAP (2-naphthylmethyl) groups using DDQ (2,3-dichloro-5,6-dicyano-1,4-benzoquinone) and removing 5 NAP groups (process 9).

compound E

[Structure of compound E]

Tenth process is obtaining aimed compound CTX1B by acid treatment of above mentioned compound E (process 10).

[Structure of CTX1B with rings labeled A–M]

CTX1B

The second one of the present invention is a novel compound represented by compound 1, which is useful for the method to prepare CTX1B. The third one of the present invention is a novel compound represented by compound 2, which is useful for the method to prepare CTX1B. The fourth one of the present invention is a novel compound represented by compound 3, which is useful for the method to prepare CTX1B. The fifth one of the present invention is a novel compound represented by compound 4, which is useful for the method to prepare CTX1B. The sixth one of the present invention is a novel compound represented by compound 5, which is useful for the method to prepare CTX1B. The seventh one of the present invention is a novel compound represented by compound 6, which is useful for the method to prepare CTX1B. The eighth one of the present invention is a novel compound represented by compound 7, which is useful for the method to prepare CTX1B. And the ninth one of the present invention is a novel compound represented by compound 8, which is useful for the method to prepare CTX1B.

EFFECT OF THE INVENTION

The offering of an effective total synthesis of CTX1B of the present invention is important from the view point that practical amount of said compound to ensure a progress in the research of biological science or a development for detection of Ciguatera poisoned fish can be supplied, and has an effect that can be practically used as a standard specimen of Ciguatera food-poisoning happened in all over the world.

PREFERRED EMBODIMENT OF THE INVENTION

The present invention will be illustrated more in detail. A. Since HIJKLM ring segments compound A (J. Org. Chem. 69, 2797-2804 (2004)), which was reported in afore mentioned non-patent document 3, has a structure corresponding to half of CTX1B, said compound A is used as an intermediate for synthesis of CTX1B. By reaction condition mentioned in following reaction formula, double bond of compound A is oxidized by osmium tetra oxide and transformed to diol, then transformed to aldehyde by oxidation cleavage by sodium periodate (at room temperature), after that, reduced to alcohol using sodium borohydride and obtain compound 1 (yield of these two processes is 91%).

Alcohol of compound 1 is transformed to compound 2 using diphenyldisulfide•tributylphosphine (at room temperature, yield is 96%).

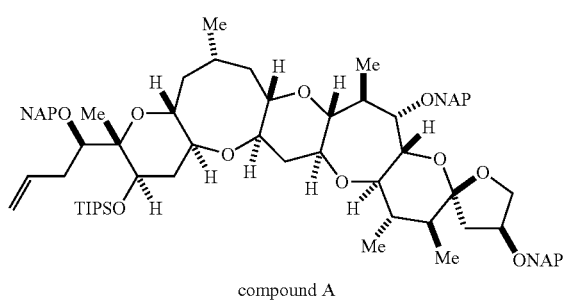

compound A

1) OsO₄, NMO
   THF/H₂O = 1,
   2 h then,
   NaIO₄
   rt, 30 min

2) NaBH₄
   MeOH/CH₂Cl₂ = 1
   0° C., 3 h
   91% (2 steps)

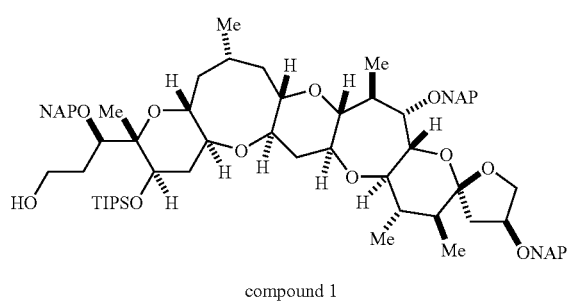

compound 1

(PhS)₂, n-BuP₃, Py
rt, 6 h, 96%

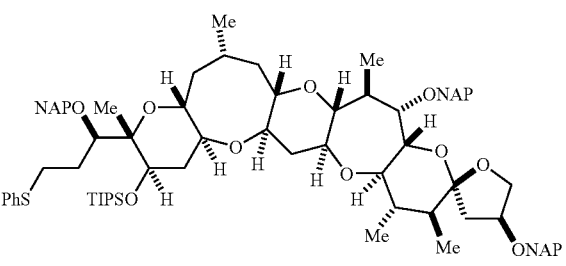

compound 2

Compound 2 is transformed to a α-chrolosulphide in 6:1 mixed solvent of carbon tetrachloride and dichloromethane using NSC and compound B is synthesized.

Then, ABCDE ring segments compound C, which is already reported in paper aforementioned non-patent document 4, J. Org. Lett., 6, 751-754 (2004)), and compound B are joined as O,S-acetal using silver triflate (AgOTf) in 1:5 mixed solvent of carbon tetrachloride and dichloromethane under the presence of DTBMP and compound 3 is obtained (yield to compound C is 63%).

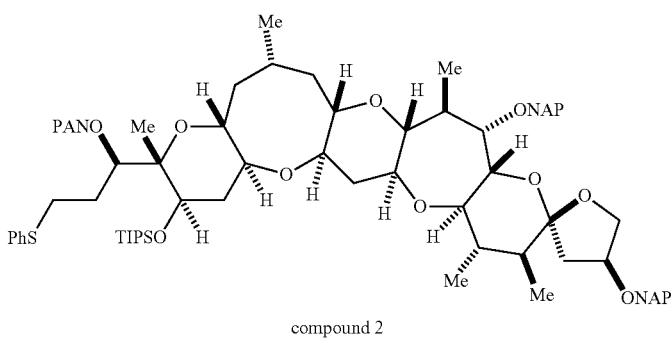

compound 2

NCS
CCl₄/CH₂Cl₂ = 6
rt, 2 h

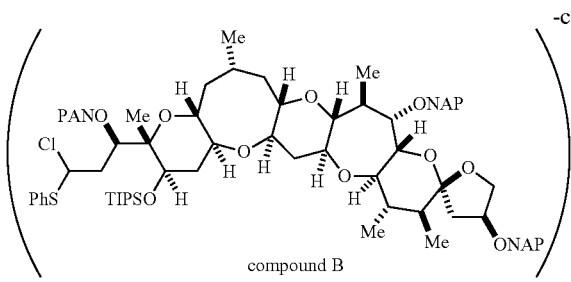

compound B

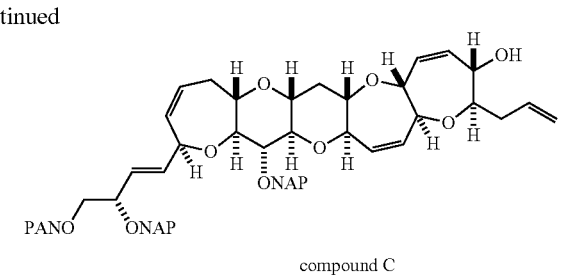

compound C

AgOTf, DTBMP
MS4A, CCl$_4$/CH$_2$Cl$_2$ = 1/5
−80° C. to −10° C., 5 h, 63%
(from compound C)

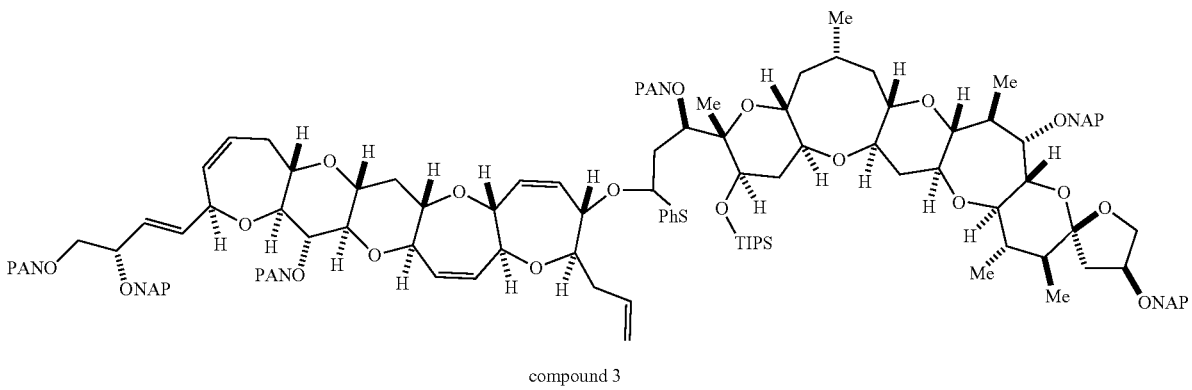

compound 3

TIPS group of compound 3 is removed by TBAF and compound 4 is formed (yield is 92%). Pentafluorophenylpropiolate acrylate is introduced into alcohol of compound 4 using pentafluorophenylpropiolate and trimethylphosphine and compound 5 is formed (yield is 94%).

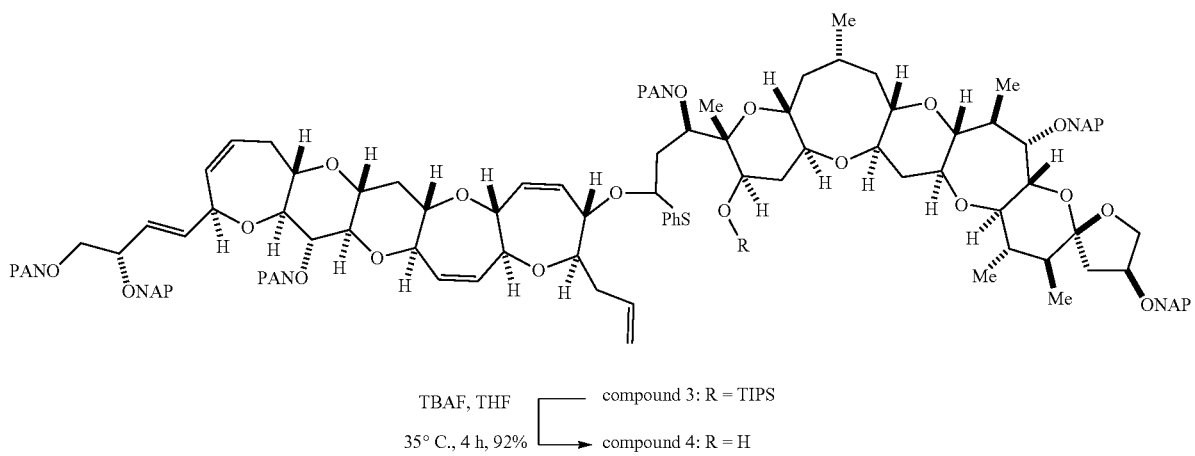

TBAF, THF
35° C., 4 h, 92% compound 3: R = TIPS
compound 4: R = H

≡—CO$_2$C$_6$F$_5$
PMe$_3$, CH$_2$Cl$_2$
rt, 2.5 h, 94%

-continued

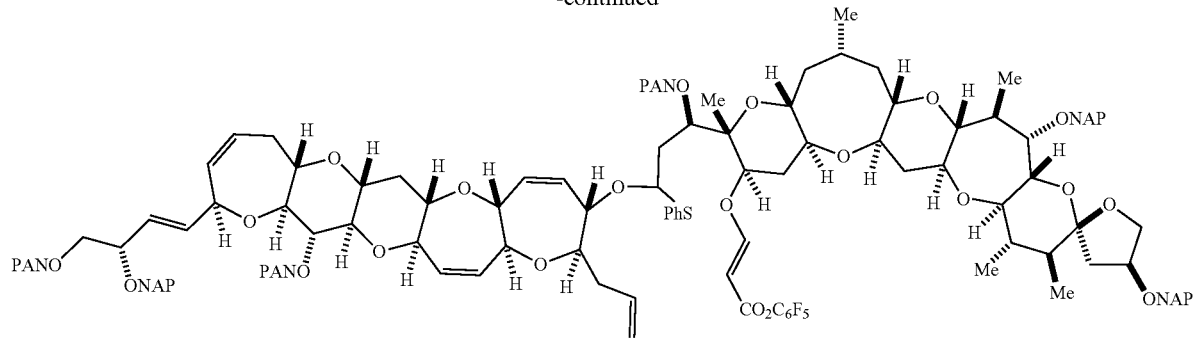

compound 5

Radical cyclizing reaction is carried out on compound 5 by treating with AIBN and tributyltin hydride in toluene at 85° C. and G ring part is formed, thus carboxylic acid compound D is obtained. In mixed solvent of benzene and methanol, trimethylsilyldiazomethane is acted to compound D so as to transform to methyl ester, and compound 6 is formed.

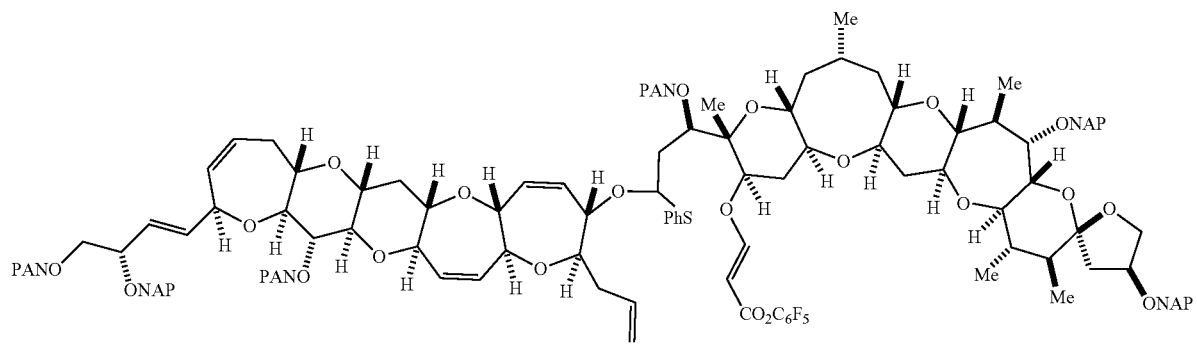

compound 5

AIBN, n-Bu$_3$SnH
toluene, 85° C., 3 h, 59%

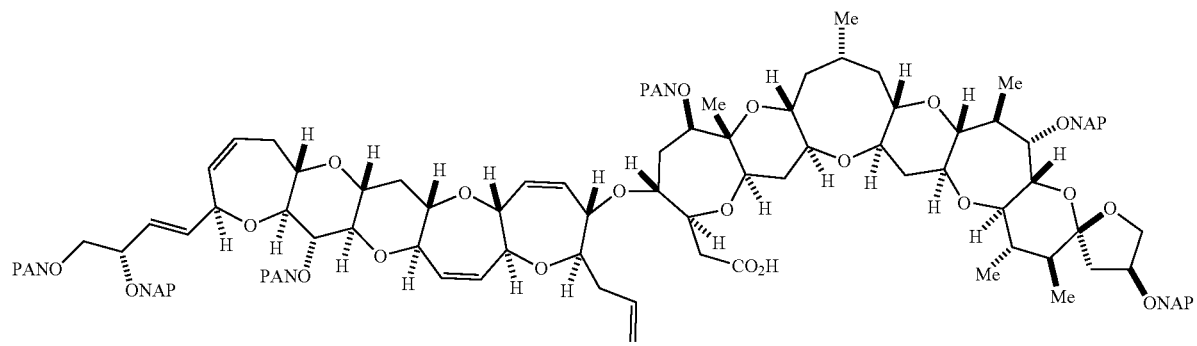

compound D

TMSCHN$_2$
benzene/MeOH = 5/2, rt
30 min, 84%

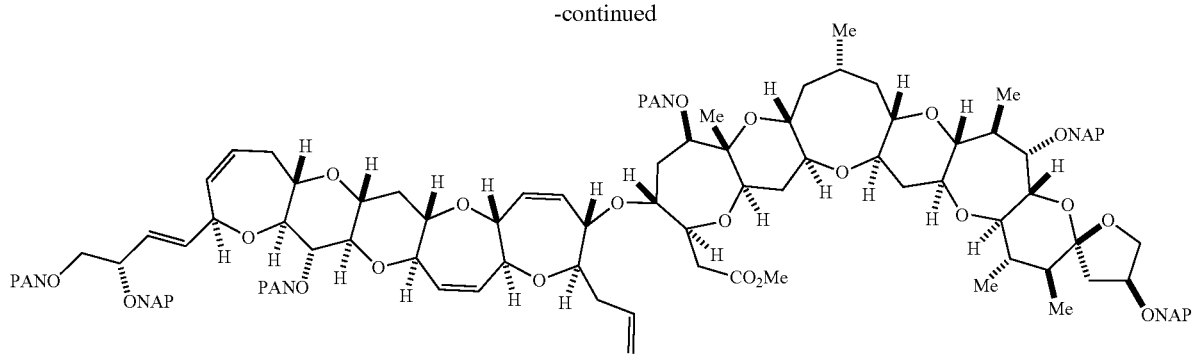

compound 6

Methyl ester of compound 6 is reduced to aldehyde by diisobutylaluminum hydride under low temperature condition, then transformed to olefin by Wittig reaction and compound 7 is formed. Grubbs catalyst is acted to compound 7 and F ring part is formed by carrying out ring closure methathesis reaction, and compound 8 is obtained.

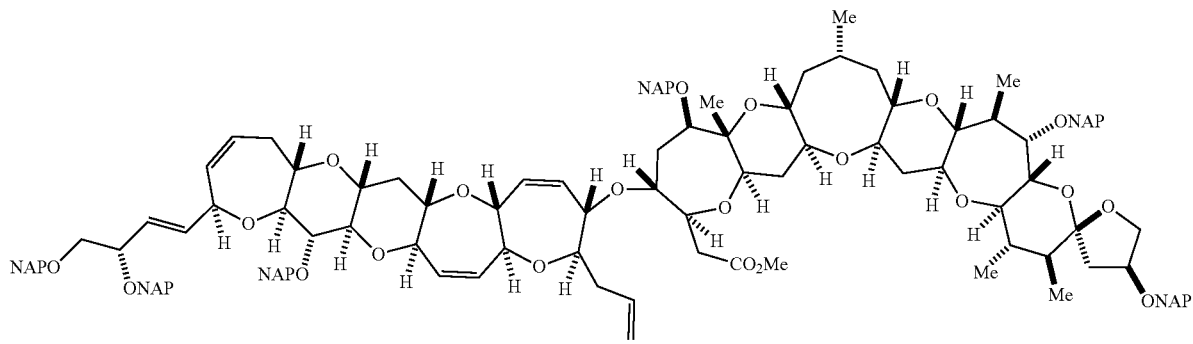

compound 6

1) DIBAL, CH$_2$Cl$_2$
   $-100°$ C. to $-90°$ C., 30 min
2) Ph$_3$CHBr, t-BuOK
   THF, $0°$ C., 30 min
   77% (2 steps)

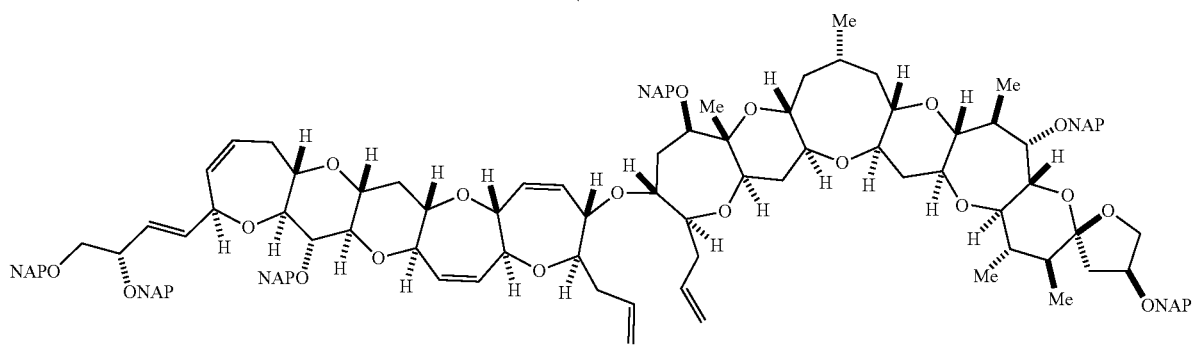

compound 7

1st. Grubbs cat. (30 mol %)
CH$_2$Cl$_2$, $40°$ C., 1 h
78% compound 8

Six NAP groups of compound 8 are oxidized using DDQ and 5 NAP groups is removed, thus compound E characterized that 1,2-diol of A ring side chain is protected by naphthylacetal is formed. Finally, compound E is treated by 1N hydrochloric acid in methanol solvent and total synthesis of CTX1B, which is aimed compound, is accomplished.

compound 8

DDQ, CH$_2$Cl$_2$/H$_2$O = 1, 45 min
then HPLC
Asahipak ODP 50-6D, CH$_3$CN/H$_2$O = 80/20
flow = 1.0ml/min, UV 254, 210 nm compound E 1N HCl, MeOH, rt, 30 min
then HPLC
Asahipak ODP 50-6D, CH$_3$CN/H$_2$O = 60/40
flow = 1.0ml/min, UV 215 nm
42% (2 steps)

EXAMPLES

More concrete synthesis will be shown as Examples, however, these Examples are shown to understand the present invention more easily and not intending the scope of the present invention.

Example 1

Synthesis of Compound 1

HIJKLM ring segments compound A (151 mg, 129 μmol) is dissolved in mixed solvent (0.1M) of THF (0.86 mL)-water (0.43 mL), then osmium tetra oxide (19 mM, t-BuOH solution, 710 μL, 13.4 μmol) and NMO (50% aqueous solution, 94 μL, 402 μmol) are added and stirred vigorously for 2 hours. To this solution, phosphoric acid buffer solution (pH=7.0, 3.0 mL, 0.04M) and sodium periodate (120 mg, 536 μmol) are added gradually and stirred at room temperature for 3 hours. Reaction is stopped by adding saturated $Na_2S_2O_3$ aqueous solution to this solution and diluted by ethyl acetate and saturated $NaHCO_3$ aqueous solution. Water phase is extracted by ethyl acetate for 3 times, and combined organic layer is washed by saturated brine, then is dried by $Na_2SO_4$. Solvent is concentrated and crude aldehyde is used to the next reaction without refining.

$CH_2Cl_2$ (5.0 mL, 0.25M) solution of aldehyde is cooled to 0° C., and sodium borohydride (25 mg, 670 μmol) is added and stirred for 30 minutes. Reaction is stopped by adding saturated $NH_4Cl$ aqueous solution into this solution and diluted by ethyl acetate. Water phase is extracted by ethyl acetate for 3 times, and combined organic layer is washed by saturated brine, then is dried by $Na_2SO_4$. Solvent is concentrated and refined by a flash column, then alcohol of compound 1 (138 mg, 1.17 μmol) is obtained. Total yield of this 2 processes is 91%. Features of compound 1 are shown in Table 1.

TABLE 1

$[\alpha]_D^{23}$ −10.3 (c 0.41, $CHCl_3$); IR (film) ν 2926, 2865, 1723, 1463, 1090 $cm^{-1}$
$^1H$ NMR (500 MHz, $CDCl_3$) δ 7.83-7.41 (21H, m, NAP × 3), 4.81 (1H, d, J = 12.0 Hz, NAP), 4.79 (1H, d, J = 12.0 Hz, NAP), 4.73 (1H, d, J = 12.0 Hz, NAP), 4.66 (1H, d, J = 12.0 Hz, NAP), 4.61 (1H, d, J = 12.0 Hz, NAP),
4.58 (1H, d, J = 12.0 Hz, NAP), 4.31 (1H, dd, J = 11.5, 5.0 Hz, H34), 4.26 (1H, m, H54), 3.97 (1H, dd, J = 9.5, 1.5 Hz, H55), 3.88-3.80 (4H, m, H30, H32, H44, H55), 3.64 (1H, m, H30), 3.61 (1H, d, J = 9.5 Hz, H48), 3.43-3.41 (2H, m, H47, H49), 3.39 (1H, ddd, J = 9.5, 3.5, 3.5 Hz, H37), 3.15 (1H, ddd, J = 11.5, 9.5, 5.0 Hz, H36), 3.10 (1H, ddd, J = 11.5, 9.5, 5.0 Hz, H42), 2.98 (1H, ddd, J = 9.5, 2.5, 2.5 Hz, H41), 2.84 (1H, dd, J = 9.0, 4.0 Hz, H45), 2.25-2.14 (6H, m, H31, H35, H43, H46, H53, H53), 1.95 (1H, m, H31), 1.89-1.77 (3H, m, H38, H39, H40), 1.73 (1H, ddd, J = 11.5, 11.5, 11.5 Hz, H35), 1.67-1.53 (4H, m, H38, H40, H50, H51), 1.39 (1H, ddd, J = 11.5, 11.5, 11.5 Hz, H43),
1.18 (3H, S, Me56), 1.09 (3H, d, J = 7.5 Hz, Me58), 1.07-1.02 (30H, m, TIPS, Me57, Me59, Me60)
$^{13}C$ NMR (125 MHz, $CDCl_3$) δ136.7, 136.3, 135.6, 133.26, 133.24, 133.1, 132.9, 132.8, 128.1, 127.9, 127.86, 127.83, 127.74, 127.72, 127.69, 127.65, 126.2, 126.14, 126.12, 126.0, 125.9, 125.8, 125.68, 125.65, 108.9, 86.7, 84.6, 82.9, 80.8, 80.0, 79.6, 78.5, 77.8, 74.1, 73.7, 72.1, 71.9, 71.8, 71.4, 71.1, 68.0, 58.7, 42.5, 41.6, 40.4, 40.0, 38.4, 38.2, 31.5, 29.9, 27.5, 22.6, 19.9, 18.4, 18.3, 18.19, 18.14, 15.9, 14.1, 14.0, 13.5, 13.4, 13.0, 12.9
MALDI-TOF MS, calcd. for $C_{74}H_{96}NaO_{10}Si$ 1199.6620 (M + $Na^+$), found for 1199.6620

Synthesis of Compound 2

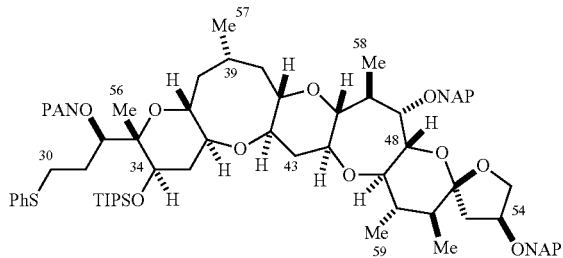

compound 2

Into pyridine (1.2 mL, 0.1M) solution of compound 1 (138 mg, 117 µmol), PhSSP (153 mg, 702 µmol) and n-PBu$_3$ (175 µL, 702 µmol) are added and stirred at room temperature for 6 hours. Reaction is stopped by adding saturated NH$_4$Cl aqueous solution into this solution and diluted by ethyl acetate. Water phase is extracted by ethyl acetate for 3 times, and combined organic layer is washed by saturated brine, then is dried by Na$_2$SO$_4$. Solvent is concentrated and refined by a flash column, then thiophenylether of compound 2 (143 mg, 113 µmol, 96%) is obtained. Features of compound 2 are shown in Table 2.

TABLE 2

$[\alpha]_D^{25}$ −3.3 (c 0.47, CHCl$_3$); IR (film) ν 2927, 2858, 1708, 1464, 1093, 1030 cm$^{-1}$
$^1$H NMR (500 MHz, CDCl$_3$) δ 7.83-7.11 (26H, m, NAP × 3, PhS), 4.81 (1H, d, J = 12.0 Hz, NAP), 4.81 (1H, d, J = 12.5 Hz, NAP), 4.76 (1H, d, J = 12.5 Hz, NAP), 4.75 (1H, d, J = 12.0 Hz, NAP), 4.62 (1H, d, J = 12.0 Hz, NAP), 4.59 (1H, d, J = 12.0 Hz, NAP), 4.27 (1H, m, H54), 4.21 (1H, dd, J = 12.0, 5.0 Hz, H34), 3.98 (1H, d, J = 9.5 Hz, H55), 3.86 (1H, ddd, J = 12.0, 9.0, 5.0 Hz, H44), 3.83 (1H, dd, J = 9.5, 5.5 Hz, H55), 3.77 (1H, dd, J = 7.5, 3.5 Hz, H32), 3.62 (1H, d, J = 9.5 Hz, H48), 3.64 (1H, m, H30), 3.44 (1H, d, J = 3.5 Hz, H47), 3.43 (1H, dd, J = 9.5, 9.5 Hz, H49), 3.30 (1H, ddd, J = 10.0, 10.0, 3.0 Hz, H37), 3.17 (1H, ddd, J = 13.5, 9.0, 4.5 Hz, H30), 3.11 (1H, ddd, J = 12.0, 10.0, 5.0 Hz, H42), 3.09 (1H, ddd, J = 12.0, 10.0, 5.0 Hz, H36), 3.00 (1H, ddd, J = 10.0, 10.0, 2.5 Hz, H41), 2.93 (1H, ddd, J = 13.5, 8.5, 7.5 Hz, H30), 2.86 (1H, dd, J = 9.0, 4.5 Hz, H45), 2.20 (1H, ddd, J = 12.0, 5.0, 5.0 Hz, H43), 2.18 (1H, m, H46), 2.16 (1H, m, H53), 2.15 (1H, m, H53), 2.13 (1H, ddd, J = 12.0, 5.0, 5.0 Hz, H35), 2.10 (1H, m, H31), 2.00 (1H, m, H31), 1.86 (1H, m, H40), 1.82 (1H, m, H39), 1.79 (1H, m, H36), 1.72 (1H, ddd, J = 12.0, 12.0, 12.0 Hz, H35), 1.61 (1H, m, H50), 1.59 (1H, m, H51), 1.56 (1H, m, H36), 1.54 (1H, m, H40), 1.39 (1H, ddd, J = 12.0, 12.0, 12.0 Hz, H43), 1.12 (3H, s, Me56), 1.09 (3H, d, J = 7.5 Hz, Me58), 1.07 (3H, d, J = 7.0 Hz, Me57), 1.06 (3H, d, J = 7.0 Hz, Me59), 1.04 (21H, m, TIPS), 1.02 (3H, m, Me60)
$^{13}$C NMR (125 MHz, CDCl$_3$) δ 136.8, 136.74, 136.17, 135.6, 133.25, 133.23, 133.1, 132.9, 132.8, 132.7, 128.7, 128.6, 128.1, 127.85, 127.83, 127.73, 127.71, 127.68, 127.63, 126.2, 126.1, 126.0, 125.98, 125.92, 125.8, 125.7, 125.68, 125.64, 125.61, 125.5, 108.9, 86.6, 84.5, 82.9, 80.9, 80.8, 80.1, 78.5, 77.8, 74.2, 73.4, 72.1, 71.8, 71.4, 71.1, 68.5, 60.4, 42.4, 41.5, 40.5, 40.0, 38.4, 38.3, 30.3, 29.6, 28.1, 27.5, 21.0, 19.9, 18.46, 18.43, 18.38, 18.34, 18.2, 18.1, 15.9, 14.17, 14.11, 13.8, 13.5, 13.4, 13.0
MALDI-TOF MS, calcd. for C$_{76}$H$_{102}$NaO$_{10}$SSi 1291.6704 (M + Na$^+$), found for 1291.6624

Synthesis of Compound 3

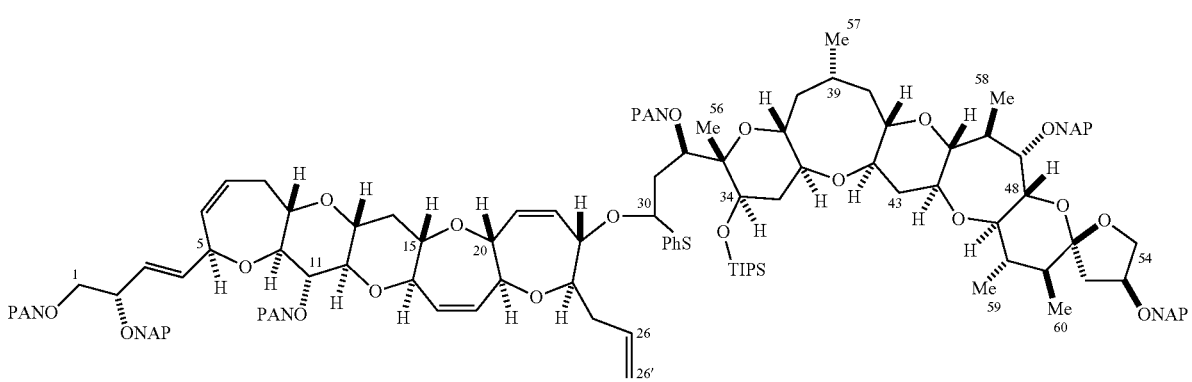

compound 3

N-chlorosuccinimide (2.67 mg, 20 μmol) is dissolved in CH$_2$Cl$_2$ (50 μL) and added into CCl$_4$ (280 μL, 0.07M) solution of compound 2 (24.6 mg, 19.4 μmol) solution, stirred at room temperature for 2 hours and compound B is formed. This solution is dropped slowly into −80° C. cooled CH$_2$Cl$_2$ solution of compound C (11.2 mg, 12.1 mol), silver triflate (7.5 mg, 32.3 μmol), DTBMP (13.3 mg, 64.5 μmol) and activated MS4A (40 mg), stirred for 2 hours and elevated the temperature to −10° C. This reacted solution is filtrated by 0° C. cooled open column and concentrated. After that, refined by a flash column and compound 3, O,S-acetal (16.6 mg, 7.57 μmol, 63%) is obtained. Features of compound 3 are shown in Table 3.

TABLE 3

[α]$_D^{23}$ 4.5 (c 1.00, CH$_2$Cl$_2$); IR (film) ν 2927, 2865, 1775, 1716, 1459, 1344, 1291, 1090, 816 cm$^{-1}$;
$^1$H NMR (500 MHz, C$_6$D$_6$) δ 8.02-6.92 (47H, m, NAP × 6, PhS), 6.11 (1H, ddd, J = 13.0, 2.5, 2.5 Hz, H22), 5.98 (1H, dd, J = 15.0, 2.5 Hz, H4), 5.93 (1H, dd, J = 15.0, 2.5 Hz, H3), 5.84 (1H, dddd, J = 17.0, 10.0, 5.5, 5.5 Hz, H26), 5.79 (1H, d, J = 11.5 Hz, H17), 5.78 (1H, d, J = 11.5 Hz, H18), 5.70 (1H, ddd, J = 11.5, 3.0, 3.0 Hz, H6), 5.61 (1H, ddd, J = 13.0, 2.5, 2.5 Hz, H21), 5.53 (1H, m, H7), 5.33 (1H, dd, J = 10.0, 3.0, 3.0 Hz, H30), 5.24 (2H, s, NAP), 5.21 (1H, d, J = 12.5 Hz, NAP), 5.14 (1H, d, J = 12.5 Hz, NAP), 5.06 (1H, dd, J = 17.0, 2.0 Hz, H26'), 4.98 (1H, dd, J = 10.0, 2.0 Hz, H26'), 4.86 (1H, d, J = 12.5 Hz, NAP), 4.82 (1H, d, J = 12.5 Hz, NAP), 4.81 (1H, d, J = 12.0 Hz, NAP), 4.62 (1H, d, J = 12.0 Hz, NAP), 4.54 (1H, m, H5), 4.51 (2H, s, NAP), 4.47 (1H, dd, J = 12.0, 5.0 Hz, H34), 4.38 (1H, dd, J = 10.0, 3.0 Hz, H32), 4.32 (2H, s, NAP), 4.23 (1H, m, H23), 4.20 (1H, m, H2), 4.18 (1H, m, H19), 4.15 (1H, m, H44), 4.08 (1H, m, H54), 4.04 (1H, d, J = 10.0 Hz, H55), 3.96 (1H, d, J = 9.5 Hz, H48), 3.91 (1H, m, H20), 3.78 (1H, dd, J = 10.0, 5.0 Hz, H55), 3.75 (1H, dd, J = 10.0, 2.0 Hz, H1), 3.73 (1H, dd, J = 9.5, 9.5 Hz, H49), 3.71 (1H, d, J = 8.0 Hz, H16), 3.67 (1H, dd, J = 9.0, 9.0 Hz, H11), 3.65 (1H, m, H24), 3.62 (1H, d, J = 3.0 Hz, H47), 3.56 (1H, dd, J = 9.0, 9.0 Hz, H10), 3.52 (1H, dd, J = 10.0, 4.5 Hz, H1), 3.32 (1H, m, H37), 3.30 (1H, ddd, J = 9.0, 9.0, 5.5 Hz, H9), 3.19 (1H, dd, J = 9.0, 9.0 Hz, H12), 3.11 (1H, m, H15), 3.10 (1H, m, H41), 3.03 (1H, dd, J = 9.5, 5.0 Hz, H45), 3.02 (1H, m, H36), 2.99 (1H, m, H42), 2.93 (1H, ddd, J = 11.5, 9.0, 4.5 Hz, H13), 2.85 (1H, m, H31), 2.59 (1H, ddd, J = 16.0, 9.0, 4.5 Hz, H8), 2.53 (1H, m, H25), 2.51 (1H, m, H31), 2.49 (1H, m, H46), 2.47 (1H, m, H43), 2.33 (1H, m, H8), 2.31 (1H, m, H35), 2.29 (1H, m, H14), 2.23 (1H, m, H53), 2.21 (1H, m, H53), 2.20 (1H, m, H25), 2.03 (1H, m, H40), 1.97 (1H, m, H50), 1.95 (1H, m, H35), 1.92 (1H, m, H38), 1.83 (1H, m, H39), 1.77 (1H, ddd, J = 12.0, 12.0, 12.0 Hz, H43), 1.67 (1H, ddd, J = 1.5, 11.5, 11.5 Hz, H14), 1.63 (1H, m, H40), 1.59 (1H, m, H38), 1.54 (1H, m, H51), 1.13 (3H, m, Me58), 1.13 (21H, m, TIPS), 1.12 (3H, m, Me56), 1.11 (3H, d, J = 6.5 Hz, Me59), 1.08 (3H, d, J = 7.0 Hz, Me60), 0.98 (3H, d, J = 7.0 Hz, Me57);
$^{13}$C NMR (125 MHz, C$_6$D$_6$) δ 176.5, 137.6, 137.5, 137.3, 136.9, 136.7, 136.43, 136.41, 135.1, 134.4, 134.2, 134.05, 133.99, 133.97, 133.95, 133.92, 133.57, 133.54, 133.52, 133.4, 133.3, 131.4, 131.1, 129.2, 129.1, 128.48, 128.45, 128.41, 128.35, 128.19, 128.16, 128.13, 128.12, 128.0, 127.7, 126.9, 126.67, 126.65, 126.57, 126.55, 126.46, 126.44, 126.34, 126.29, 126.23, 126.20, 126.15, 126.12, 126.05, 126.02, 126.00, 125.98, 125.92, 125.86, 125.79, 117.4, 109.5, 89.9, 87.3, 85.6, 84.6, 83.5, 83.1, 82.2, 81.8, 81.5, 80.8, 80.5, 79.9, 79.3, 79.2, 79.1, 78.6, 78.2, 76.8, 75.3, 74.7, 74.3, 73.9, 73.5, 73.1, 72.9, 72.8, 71.7, 71.3, 71.1, 68.9, 68.1, 60.1, 43.2, 42.2, 41.5, 40.9, 39.2, 39.1, 38.2, 37.6, 34.9, 34.7, 31.7, 30.2, 29.2, 28.1, 20.2, 18.73, 18.69, 16.3, 14.4, 13.9, 13.6, 11.2
MALDI-TOF MS, calcd. for C$_{139}$H$_{158}$NaO$_{19}$SSi 2214.0780 (M + Na$^+$), found for 2213.9349

Synthesis of Compound 4 compound 4

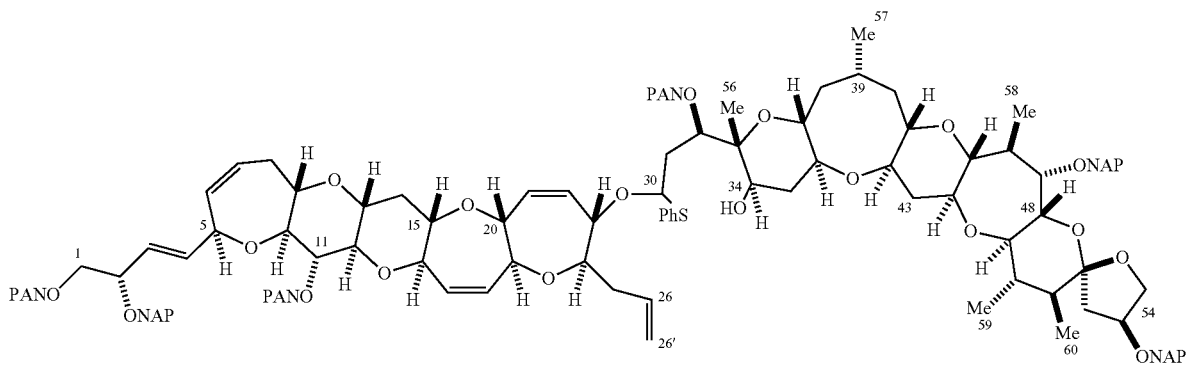

TBAF (1.0M THF solution, 23 μL, 23 μmol) is added to THF (300 μL, 0.02M) solution of compound 3 (12.6 mg, 5.74 μmol) and stirred at 35° C. for 4 hours. After this solution is concentrated, refined using a flush column and alcohol of compound 4 (10.78 mg, 5.30 μmol, 92%) is obtained. Features of compound 4 are shown in Table 4.

TABLE 4

$[\alpha]_D^{23}$ 10.2 (c 1.00, CH$_2$Cl$_2$); IR (film) ν 3221, 2926, 1775, 1715, 1456, 1347, 1177, 1088, 817 cm$^{-1}$;
$^1$H NMR (500 MHz, C$_6$D$_6$) δ 7.99-6.98 (47H, m, NAP × 6, PhS), 6.14 (1H, ddd, J = 13.0, 3.0, 3.0 Hz, H22), 5.99 (1H, dd, J = 16.0, 1.5 Hz, H4), 5.96 (1H, dd, J = 16.0, 1.5 Hz, H3), 5.86 (1H, d, J = 12.5 Hz, H17), 5.84 (1H, d, J = 12.5 Hz, H18), 5.78 (1H, dddd, J = 17.0, 10.5, 6.5, 6.5 Hz, H26), 5.71 (1H, ddd, J = 13.0, 3.0, 3.0 Hz, H21), 5.69 (1H, ddd, J = 11.5, 3.0, 3.0 Hz, H6), 5.52 (1H, dddd, J = 11.5, 7.0, 4.0, 3.5 Hz, H7), 5.23 (2H, s, NAP), 5.20 (1H, dd, J = 7.0, 6.5 Hz, H30), 5.01 (1H, dd, J = 17.0, 2.5 Hz, H26'), 4.98 (1H, dd, J = 10.0, 2.5 Hz, H26'), 4.88 (1H, d, J = 12.5 Hz, NAP), 4.85 (1H, d, J = 12.5 Hz, NAP), 4.82 (1H, d, J = 12.0 Hz, NAP), 4.70 (1H, d, J = 12.0 Hz, NAP), 4.65 (1H, d, J = 12.0 Hz, NAP), 4.62 (1H, d, J = 12.0 Hz, NAP), 4.53 (1H, m, H5), 4.52 (1H, d, J = 12.0 Hz, NAP), 4.49 (1H, d, J = 12.0 Hz, NAP), 4.40 (1H, ddd, J = 8.0, 3.0, 3.0 Hz, H23), 4.34 (2H, s, NAP), 4.28 (1H, dd, J = 9.0, 3.0 Hz, H19), 4.21 (1H, m, H44), 4.19 (1H, m, H2), 4.09 (1H, m, H54), 4.07 (1H, d, J = 9.5 Hz, H55), 4.01 (1H, m, H20), 3.96 (1H, d, J = 8.5 Hz, H48), 3.96 (1H, m, H32), 3.95 (1H, m, H34), 3.83 (1H, d, J = 8.0 Hz, H16), 3.82 (1H, dd, J = 8.5, 8.5 Hz, H49), 3.81 (1H, dd, J = 9.5, 4.5 Hz, H55), 3.70 (1H, dd, J = 9.0, 9.0 Hz, H11), 3.69 (1H, dd, J = 10.5, 3.0 Hz, H1), 3.66 (1H, d, J = 3.0 Hz, H47), 3.61 (1H, ddd, J = 8.0, 4.0 Hz, H24), 3.53 (1H, dd, J = 10.5, 4.5 Hz, H1), 3.51 (1H, dd, J = 9.0, 9.0 Hz, H10), 3.30 (1H, m, H9), 3.28 (1H, m, H37), 3.16 (1H, dd, J = 9.0, 9.0 Hz, H12), 3.13 (1H, m, H15), 3.07 (1H, dd, J = 9.5, 4.5 Hz, H45), 3.05 (1H, m, H41), 2.92 (1H, ddd, J = 11.5, 9.0, 4.0 Hz, H13), 2.88 (1H, m, H42), 2.71 (1H, m, H31), 2.70 (1H, m, H36), 2.59 (1H, ddd, J = 15.5, 8.0, 4.0 Hz, H8), 2.56 (1H, m, H46), 2.49 (1H, m, H25), 2.46 (1H, m, H31), 2.41 (1H, ddd, J = 13.0, 5.0, 5.0 Hz, H43), 2.32 (1H, ddd, J = 11.5, 4.0, 4.0 Hz, H14), 2.29 (1H, m, H8), 2.24 (1H, m, H53), 2.23 (1H, m, H53), 2.20 (1H, m, H25), 2.16 (1H, m, H35), 2.05 (1H, m, H50), 2.02 (1H, m, H40), 1.78 (1H, m, H39), 1.76 (1H, m, H35), 1.72 (1H, ddd, J = 12.5, 12.5, 12.5 Hz, H43), 1.70 (1H, ddd, J = 1.5, 11.5, 11.5 Hz, H14), 1.60 (1H, m, H38), 1.56 (1H, m, H51), 1.52 (1H, m, H40), 1.32 (3H, s, Me56), 1.27 (3H, d, J = 6.5 Hz, Me59), 1.18 (1H, m, H38), 1.17 (3H, d, J = 7.5 Hz, Me60), 1.16 (3H, d, J = 6.5 Hz, Me58), 0.93 (3H, d, J = 7.5 Hz, Me57)
$^{13}$C NMR (125 MHz, C$_6$D$_6$) δ 176.4, 137.6, 137.3, 136.9, 136.7, 136.4, 135.4, 135.0, 134.4, 134.00, 133.99, 133.97, 133.95, 133.94, 133.8, 133.7, 133.58, 133.55, 133.52, 132.8, 132.6, 131.0, 129.3, 129.1, 128.8, 128.47, 128.42, 128.35, 128.2, 128.0, 127.7, 127.5, 126.88, 126.85, 126.67, 126.65, 126.59, 126.56, 126.52, 126.49, 126.47, 126.45, 126.38, 126.33, 126.29, 126.23, 126.14, 126.08, 126.00, 125.93, 125.89, 117.4, 109.6, 89.8 87.34, 87.27, 85.57, 85.52, 84.4, 83.8, 83.59, 83.54, 83.49, 83.1, 82.2, 81.8, 81.5, 80.9, 80.04, 79.99, 79.2, 78.6, 77.5, 76.8, 75.4, 74.9, 73.9, 73.6, 73.5, 72.9, 71.7, 71.3, 71.1, 67.5, 46.7, 46.2, 43.3, 42.3, 41.3, 40.8, 39.2, 38.5, 37.8, 37.6, 37.3, 34.9, 32.0, 30.2, 28.6, 27.9, 23.0, 20.2, 16.3, 14.4;
MALDI-TOF MS, calcd. for C$_{130}$H$_{138}$NaO$_{19}$S 2057.9451 (M + Na$^+$), found for 2057.5975

Synthesis of Compound 5

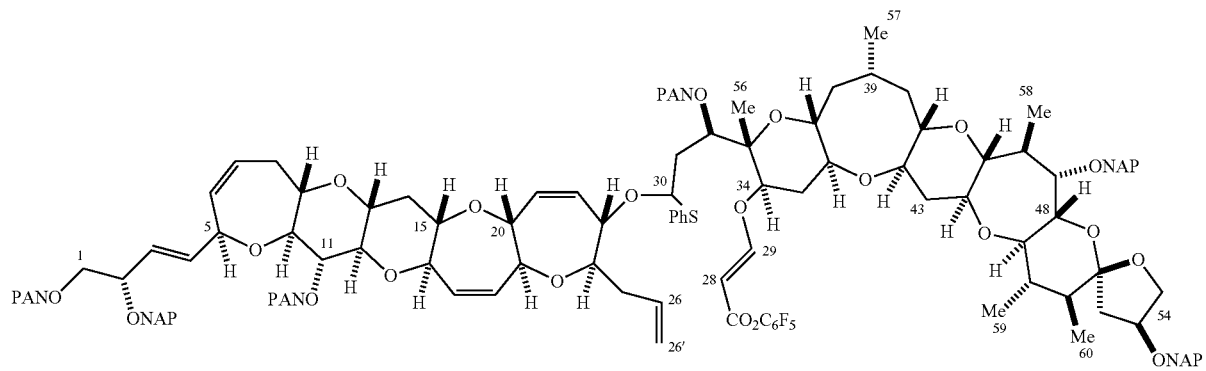

compound 5

Into CH$_2$Cl$_2$ (300 µL, 0.02M) solution of compound 4 (6.7 mg, 3.29 µmol) and pentaphenylpropiorate (3.1 mg, 13.2 µmol), PMe3 (1.0M THF solution, 6.6 µL, 6.6 µmol) is added and stirred at room temperature for 30 minutes. Further, same process to add same equivalent of pentaphenylpropiorate and PMe3 and to stir at room temperature for 30 minutes is repeated for 4 times. After this solution is concentrated, refined using a flush column and acrylate of compound 5 (7.0 mg, 3.08 µmol, 94%) is obtained. Features of compound 5 are shown in Table 5.

TABLE 5

[α]$_D^{24}$ -6.7 (c 1.00, CH$_2$Cl$_2$); IR (film) ν 3055, 2925, 1750, 1637, 1520, 1457, 1088, 817 cm$^{-1}$;
$^1$H NMR (500 MHz, C$_6$D$_6$) δ 7.99-7.00 (47H, m, NAP × 6, PhS), 7.69 (1H, d, J = 12.0 Hz, H29), 6.14 (1H, ddd, J = 12.5, 2.5, 2.5 Hz, H22), 5.99 (1H, dd, J = 16.0, 2.5 Hz, H4), 5.96 (1H, dd, J = 16.0, 2.5 Hz, H3), 5.88 (1H, dddd, J = 17.0, 10.5, 7.0, 7.0 Hz, H26), 5.84 (1H, d, J = 13.0 Hz, H17), 5.82 (1H, d, J = 13.0 Hz, H18), 5.69 (1H, ddd, J = 12.5, 2.5, 2.5 Hz, H21), 5.67 (1H, ddd, J = 13.0, 2.0, 2.0 Hz, H6), 5.58 (1H, d, J = 12.0 Hz, H28), 5.53 (1H, m, H7), 5.26 (1H, dd, J = 10.0, 4.5 Hz, H30), 5.24 (2H, s, NAP), 5.10 (1H, dd, J = 17.0, 2.0 Hz, H26'), 4.98 (1H, dd, J = 10.5, 2.0 Hz, H26'), 5.00 (1H, d, J = 11.5 Hz, NAP), 4.92 (1H, d, J = 11.5 Hz, NAP), 4.85 (2H, s, NAP), 4.81 (1H, d, J = 12.0 Hz, NAP), 4.62 (1H, d, J = 12.0 Hz, NAP), 4.53 (1H, m, H5), 4.51 (2H, s, NAP), 4.33 (2H, s, NAP), 4.30 (1H, m, H23), 4.23 (1H, m, H44), 4.21 (1H, m, H2), 4.18 (1H, m, H19), 4.09 (1H, m, H54), 4.06 (1H, m, H34), 3.99 (1H, d, J = 9.0 Hz, H48), 3.98 (1H, m, H20), 3.97 (1H, m, H32), 3.96 (1H, m, H55), 3.81 (1H, dd, J = 9.0, 9.0 Hz, H49), 3.80 (1H, dd, J = 9.5, 4.5 Hz, H55), 3.77 (1H, d, J = 10.0 Hz, H16), 3.71 (1H, dd, J = 9.0, 9.0 Hz, H11), 3.68 (1H, dd, J = 10.0, 7.0 Hz, H1), 3.66 (1H, d, J = 3.5 Hz, H47), 3.61 (1H, m, H24), 3.56 (1H, dd, J = 9.0, 9.0 Hz, H10), 3.52 (1H, dd, J = 10.0, 4.0 Hz, H1), 3.31 (1H, ddd, J = 9.0, 9.0, 4.5 Hz, H9), 3.21 (1H, m, H37), 3.20 (1H, dd, J = 9.0, 9.0 Hz, H12), 3.12 (1H, ddd, J = 11.5, 10.0, 5.0 Hz, H15), 3.06 (1H, dd, J = 9.5, 5.0 Hz, H45), 3.03 (1H, m, H41), 2.92 (1H, ddd, J = 11.5, 9.0, 5.0 Hz, H13), 2.89 (1H, m, H42), 2.73 (1H, m, H36), 2.62 (1H, m, H8), 2.60 (1H, m, H31), 2.57 (1H, m, H46), 2.54 (1H, m, H25), 2.40 (1H, m, H31), 2.35 (1H, m, H8), 2.32 (1H, m, H43), 2.29 (1H, m, H14), 2.27 (1H, m, H25), 2.23 (1H, m, H53), 2.22 (1H, m, H53), 2.03 (1H, m, H50), 2.00 (1H, m, H40), 1.86 (1H, m, H35), 1.76 (1H, m, H38), 1.72 (1H, m, H39), 1.68 (1H, ddd, J = 11.5, 11.5, 11.5 Hz, H43), 1.68 (1H, ddd, J = 1.5, 11.5, 11.5 Hz, H14), 1.59 (1H, m, H35), 1.56 (1H, m, H40), 1.54 (1H, m, H51), 1.36 (1H, m, H38), 1.25 (3H, d, J = 6.0 Hz, Me59), 1.16 (3H, d, J = 7.5 Hz, Me58), 1.14 (3H, d, J = 7.0 Hz, Me60), 1.02 (3H, s, Me56), 0.91 (3H, d, J = 7.5 Hz, Me57);
$^{13}$C NMR (125 MHz, C$_6$D$_6$) δ 165.21, 163.52, 142.9, 142.8, 141.6, 140.9, 140.4, 139.2, 139.1, 137.9, 137.6, 137.1, 136.9, 136.7, 136.5, 136.4, 135.4, 135.0, 134.4, 134.00, 133.99, 133.97, 133.95, 133.93, 133.91, 133.58, 133.56, 133.52, 133.47, 133.37, 131.6, 130.9, 129.4, 129.3, 129.1, 128.7, 128.6, 128.5, 128.42, 128.38, 128.37, 128.35, 128.14, 128.12, 128.0, 126.9, 126.8, 126.65, 126.64, 126.60, 126.58, 126.55, 126.52, 126.48, 126.46, 126.39, 126.37, 126.29, 126.27, 126.23, 126.22, 126.15, 126.10, 125.99, 125.92, 125.88, 125.75, 125.70, 117.6, 109.5, 95.7, 89.0 87.4, 87.3, 85.5, 84.6, 83.7, 83.5, 83.4, 82.4, 82.3, 81.8, 81.7, 81.5, 80.8, 79.34, 79.30, 79.2, 79.1, 78.6, 78.0, 76.8, 75.4, 74.8, 74.4, 73.9, 73.8, 73.6, 73.5, 72.9, 72.8, 71.8, 71.3, 71.1, 46.57, 46.0, 43.3, 42.2, 41.2, 40.9, 39.2, 38.2, 37.6, 36.5, 34.9, 34.7, 30.5, 30.2, 28.4, 27.9, 20.2, 16.3, 14.0, 13.7;
MALDI-TOF MS, calcd. for C$_{139}$H$_{139}$F$_5$NaO$_{21}$S 2293.9347 (M + Na$^+$), found for 2293.9377

Synthesis of Compound 6

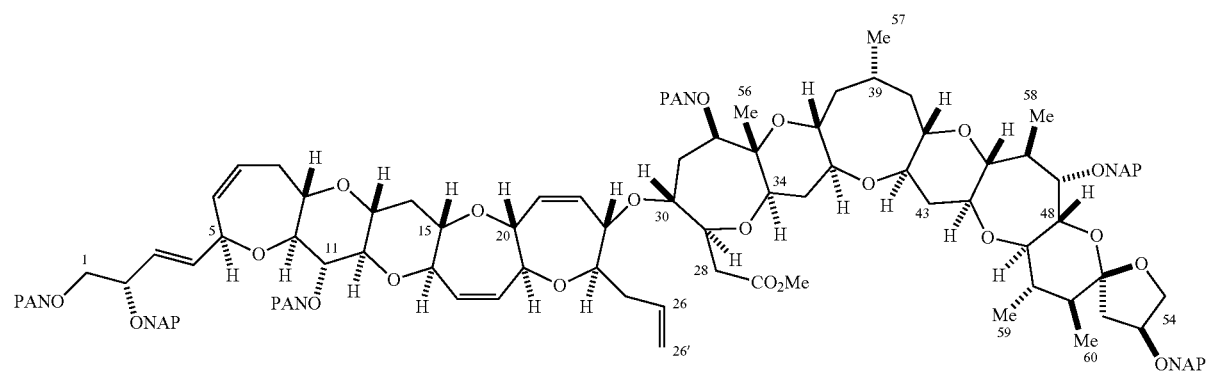

compound 6

Degassed toluene (4.3 mL, 0.001M) solution of compound 5 (6.7 mg, 3.29 μmol), AIBN (7.1 mg, 43 μmol) and n-Bu$_3$SnH (58 μL, 215 μmol) is heated to 85° C. and stirred for 3 hours. After this solution is cooled down, refined directly using a flush column and carboxylic acid of compound D (5.0 mg, 2.50 μmol, 59%) is obtained. Compound D is not refined more and used to the next reaction.

TMSCHN$_2$ (2.0M hexane solution, 13 μL, 25 μmol) is added into mixed solution (0.01M) of benzene (0.86 mL) methanol (0.43 mL) of carboxylic acid (5.0 mg, 2.50 μmol) of compound D and stirred for 30 minutes, This solution is diluted by benzene and water, and reaction is stopped by dropping acetic acid. Ethyl acetate and saturated NaHCO$_3$ aqueous solution, and water phase is extracted by ethyl acetate for 3 times. Organic layer is washed by saturated brine and dried by Na$_2$SO$_4$. Solvent is concentrated, refined by a flush column and methyl ester (4.2 mg, 2.09 μmol, 84%) of compound 6 is obtained. Features of compound 6 are shown in Table 6.

TABLE 6

$[\alpha]_D^{25}$ 10.6 (c 0.50, CH$_2$Cl$_2$); IR (film) ν 2924, 2854, 1738, 1456, 1334, 1270, 1089, 817 cm$^{-1}$;
$^1$H NMR (500 MHz, C$_6$D$_6$) δ 7.99-7.01 (42H, m, NAP × 6), 6.00 (1H, dd, J = 16.0, 2.0 Hz, H4), 5.96 (1H, dd, J = 16.0, 2.0 Hz, H3), 5.95 (1H, dddd, J = 17.0, 10.5, 7.0, 7.0 Hz, H26), 5.86 (1H, d, J = 13.0 Hz, H17), 5.84 (1H, d, J = 13.0 Hz, H18), 5.69 (1H, ddd, J = 11.0, 3.0, 3.0 Hz, H6), 5.53 (1H, d, J = 11.0 Hz, H21), 5.52 (1H, m, H7), 5.51 (1H, d, J = 11.0 Hz, H22), 5.23 (2H, s, NAP), 5.23 (1H, d, J = 12.5 Hz, NAP), 5.17 (1H, dd, J = 17.0, 3.0 Hz, H26'), 5.07 (1H, dd, J = 10.5, 3.0 Hz, H26'), 5.01 (1H, d, J = 12.5 Hz, NAP), 4.87 (1H, d, J = 12.5 Hz, NAP), 4.84 (1H, d, J = 12.5 Hz, NAP), 4.81 (1H, d, J = 12.0 Hz, NAP), 4.62 (1H, d, J = 12.0 Hz, NAP), 4.54 (1H, m, H5), 4.51 (2H, s, NAP), 5.42 (1H, dd, J = 7.0, 7.0 Hz, H29), 4.33 (2H, s, NAP), 4.27 (1H, d, J = 9.0 Hz, H19), 4.19 (1H, m, H44), 4.17 (1H, m, H2), 4.09 (1H, m, H54), 4.06 (1H, d, J = 10.5 Hz, H30), 3.99 (1H, d, J = 9.5 Hz, H23), 3.98 (1H, m, H55), 3.96 (1H, d, J = 9.0 Hz, H20), 3.83 (1H, d, J = 10.0 Hz, H16), 3.81 (1H, m, H55), 3.80 (1H, m, H32), 3.69 (1H, dd, J = 9.0, 3.5 Hz, H1), 3.68 (1H, dd, J = 9.0, 9.0 Hz, H11), 3.68 (1H, d, J = 9.0 Hz, H48), 3.65 (1H, d, J = 3.0 Hz, H47), 3.63 (1H, m, H34), 3.60 (1H, m, H24), 3.53 (1H, dd, J = 9.0, 3.5 Hz, H1), 3.52 (1H, dd, J = 9.0, 9.0 Hz, H49), 3.49 (1H, m, H37), 3.43 (1H, dd, J = 9.0, 9.0 Hz, H10), 3.31 (3H, s, MeO), 3.30 (1H, m, H9), 3.15 (1H, ddd, J = 11.5, 10.0, 4.5 Hz, H15), 3.10 (1H, m, H41), 3.09 (1H, dd, J = 9.0, 9.0 Hz, H12), 3.06 (1H, dd, J = 9.5, 4.5 Hz, H45), 2.98 (1H, m, H36), 2.94 (1H, m, H42), 2.92 (1H, m, H13), 2.58 (1H, m, H8), 2.57 (1H, m, H25), 2.55 (1H, m, H46), 2.44 (1H, dd, J = 11.0, 7.0 Hz, H28), 2.40 (1H, m, H14), 2.38 (1H, m, H25), 2.36 (1H, m, H43), 2.34 (1H, m, H8), 2.24 (1H, m, H53), 2.23 (1H, m, H53), 2.14 (1H, dd, J = 11.0, 7.0 Hz, H28), 2.11 (1H, m, H35), 2.08 (1H, m, H50), 2.07 (1H, m, H31), 2.03 (1H, m, H38), 2.01 (1H, m, H40), 1.89 (1H, m, H31), 1.86 (1H, m, H35), 1.85 (1H, m, H39), 1.72 (1H, ddd, J = 11.5, 11.5, 11.5 Hz, H43), 1.70 (1H, ddd, J = 1.5, 11.5, 11.5 Hz, H14), 1.65 (1H, m, H40), 1.59 (1H, m, H38), 1.57 (1H, m, H51), 1.29 (3H, s, Me56), 1.26 (3H, d, J = 6.0 Hz, Me59), 1.15 (3H, d, J = 6.5 Hz, Me58), 1.10 (3H, d, J = 8.0 Hz, Me60), 0.96 (3H, d, J = 7.0 Hz, Me57);
$^{13}$C NMR (125 MHz, C$_6$D$_6$) δ 170.80, 137.9, 137.7, 137.3, 136.9, 136.7, 136.5, 135.3, 135.2, 134.4, 134.3, 134.2, 134.04, 133.99, 133.96, 133.94, 133.61, 133.59, 133.55, 133.53, 131.4, 130.0, 129.3, 129.2, 128.6, 128.46, 128.42, 128.38, 128.35, 128.30, 128.16, 128.14, 128.0, 126.9, 126.8, 126.66, 126.63, 126.58, 126.55, 126.47, 126.44, 126.35, 126.29, 126.22, 126.13, 126.06, 125.99, 125.94, 125.88, 125.7, 117.4, 109.5, 87.4, 87.1, 85.6, 84.2, 83.8, 83.4, 82.4, 82.2, 81.74, 81.66, 81.2, 80.9, 80.26, 80.22, 80.1, 79.4, 79.22, 79.18, 78.6, 78.5, 76.8, 75.3, 74.9, 74.1, 73.9, 73.6, 73.5, 72.9, 72.8, 71.7, 71.3, 71.1, 47.2, 46.3, 43.3, 42.3, 41.4, 40.7, 39.9, 39.2, 38.5, 37.6, 36.1, 34.9, 32.6, 32.4, 32.0, 28.2, 27.1, 23.1, 20.2, 17.3, 16.4, 14.0, 13.8, 9.7;
MALDI-TOF MS, calcd. for C$_{128}$H$_{138}$NaO$_{21}$ 2033.9628 (M + Na$^+$), found for 2033.9634

Synthesis of Compound 7

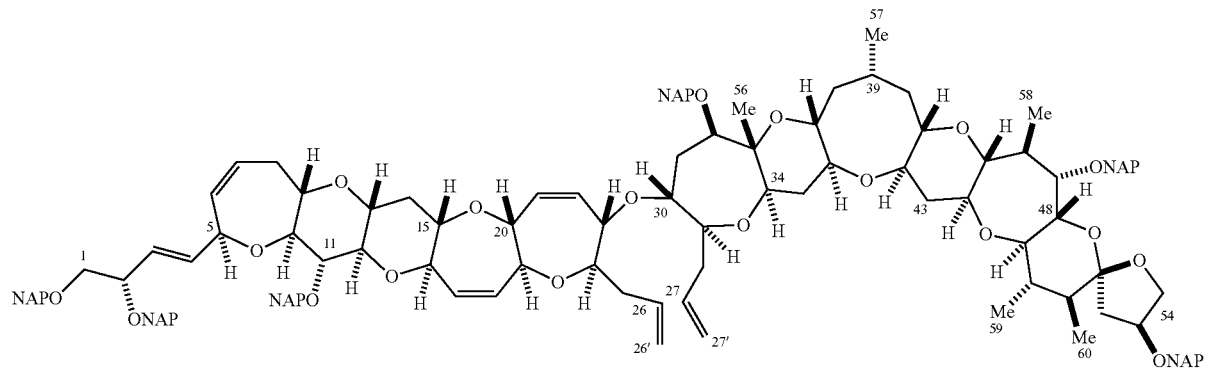

compound 7

DIBAL solution (0.9M hexane solution, 17 μL, 15.1 μmol) is dropped slowly to compound 6 (3.2 mg, 1.51 μmol), which is cooled down to −100° C., stirred for 30 minutes and elevate the temperature to −90° C. Reaction is stopped by adding Ethyl acetate and saturated NH$_4$Cl aqueous solution and diluted by ethyl acetate. Water layer is extracted by ethyl acetate for 3 times and combined organic layer is washed by saturated brine and dried by Na$_2$SO$_4$. Solvent is concentrated and crude aldehyde is obtained. This aldehyde is not refined and used in next reaction.
THF (1.0 mL, 0.001M) of triphenylphosphonium bromide (54 mg, 151 μmol) is treated with t-BuOK (8.4 mg, 75 μmol) at 0° C., and mixture is stirred at 0° C. for 20 minutes. THF solution (0.5 mL) of aldehyde is introduced and is stirred at 0° C. for 30 minutes. Reaction is stopped by adding saturated NH$_4$Cl aqueous solution and water solution is extracted by ethyl acetate. Organic layer is washed with saturated brine, then dried by Na$_2$SO$_4$. Solvent is concentrated and refined by a flush column and hexaene (2.3 mg, 1.16 μmol, total of two process is 77%) of compound 7 is obtained. Features of compound 7 are shown in Table 7.

TABLE 7

$[\alpha]D^{27}$ 2.2 (c 0.50, CH$_2$Cl$_2$); IR (film) v 2924, 1727, 1514, 1438, 1262, 1175, 1089, 818 cm$^{-1}$;
$^1$H NMR (500 MHz, C$_6$D$_6$) δ 7.99-7.01 (42H, m, NAP × 6), 5.99 (1H, m, H4), 5.97 (1H, m, H3), 5.92 (1H, dddd, J = 17.0, 10.0, 7.0, 7.0 Hz, H26), 5.88 (1H, dddd, J = 17.0, 10.5, 7.0, 7.0 Hz, H27), 5.86 (1H, d, J = 12.0 Hz, H17), 5.84 (1H, d, J = 12.0 Hz, H18), 5.70 (1H, ddd, J = 11.5, 3.0, 3.0 Hz, H6), 5.53 (1H, m, H7), 5.51 (1H, d, J = 13.0 Hz, H21), 5.46 (1H, d, J = 13.0 Hz, H22), 5.24 (2H, s, NAP), 5.20 (1H, d, J = 12.0 Hz, NAP), 5.13 (1H, dd, J = 17.0, 2.5 Hz, H26'), 5.06 (1H, dd, J = 10.0, 2.5 Hz, H26'), 5.05 (1H, dd, J = 10.5, 2.0 Hz, H27'), 5.04 (1H, d, J = 12.0 Hz, NAP), 5.01 (1H, dd, J = 17.0, 2.5 Hz, H27'), 4.86 (1H, d, J = 12.5 Hz, NAP), 4.83 (1H, d, J = 12.5 Hz, NAP), 4.81 (1H, d, J = 12.5 Hz, NAP), 4.62 (1H, d, J = 12.5 Hz, NAP), 4.54 (1H, m, H5), 4.51 (2H, s, NAP), 4.33 (2H, s, NAP), 4.20 (1H, m, H2), 4.18 (1H, d, J = 9.0 Hz, H19), 4.17 (1H, m, H44), 4.10 (1H, m, H30), 4.08 (1H, m, H54), 4.06 (1H, m, H55), 3.99 (1H, d, J = 9.5 Hz, H48), 3.94 (1H, d, J = 9.0 Hz, H20), 3.89 (1H, dd, J = 7.0, 7.0 Hz, H29), 3.83 (1H, d, J = 9.5 Hz, H16), 3.81 (1H, m, H55), 3.80 (1H, dd, J = 9.5, 9.5 Hz, H49), 3.77 (1H, d, J = 9.0 Hz, H23), 3.70 (1H, dd, J = 9.0, 3.5 Hz, H11), 3.69 (1H, dd, J = 10.5, 4.0 Hz, H1), 3.66 (1H, d, J = 3.5 Hz, H47), 3.57 (1H, dd, J = 8.5, 4.5 Hz, H34), 3.54 (1H, m, H24), 3.52 (1H, dd, J = 10.5, 4.0 Hz, H1), 3.52 (1H, m, H32), 3.51 (1H, m, H37), 3.48 (1H, dd, J = 9.0, 9.0 Hz, H10), 3.29 (1H, ddd, J = 9.0, 9.0, 4.0 Hz, H9), 3.16 (1H, ddd, J = 11.5, 9.5, 4.5 Hz, H15), 3.14 (1H, dd, J = 9.0, 9.0 Hz, H12), 3.11 (1H, m, H41), 3.06 (1H, dd, J = 8.5, 4.5 Hz, H45), 2.98 (1H, m, H36), 2.96 (1H, m, H42), 2.93 (1H, m, H13), 2.58 (1H, ddd, J = 16.0, 9.0, 4.5 Hz, H8), 2.55 (1H, m, H46), 2.53 (1H, m, H25), 2.41 (1H, ddd, J = 11.5, 4.5, 4.5 Hz, H43), 2.35 (1H, ddd, J = 11.5, 4.5, 4.5 Hz, H14), 2.29 (1H, m, H8), 2.27 (1H, m, H25), 2.24 (1H, m, H53), 2.23 (1H, m, H53), 2.22 (1H, m, H28), 2.14 (1H, m, H31), 2.13 (1H, m, H35), 2.07 (1H, m, H38), 2.06 (1H, m, H40), 2.04 (1H, m, H50), 2.02 (1H, m, H28), 1.96 (1H, m, H31), 1.93 (1H, m, H35), 1.90 (1H, m, H39), 1.73 (1H, ddd, J = 11.5, 11.5, 11.5 Hz, H43), 1.71 (1H, ddd, J = 1.5, 11.5, 11.5 Hz, H14), 1.65 (1H, m, H40), 1.59 (1H, m, H38), 1.56 (1H, m, H51), 1.27 (3H, d, J = 7.0 Hz, Me59), 1.25 (3H, s, Me56), 1.23 (3H, d, J = 7.5 Hz, Me60), 1.22 (3H, d, J = 6.5 Hz, Me58), 0.96 (3H, d, J = 6.0 Hz, Me57);
$^{13}$C NMR (125 MHz, C$_6$D$_6$) δ 137.6, 137.3, 136.9, 136.7, 136.5, 135.4, 135.2, 135.0, 134.4, 134.2, 134.1, 134.04, 134.01, 133.99, 133.98, 133.96, 133.95, 133.92, 133.59, 133.55, 133.53, 133.31, 131.5, 131.1, 130.8, 130.4, 129.3, 129.2, 128.47, 128.42, 128.35, 128.2, 126.9, 126.66, 126.65, 126.58, 126.56, 126.54, 126.48, 126.45, 126.34, 126.29, 126.24, 126.23, 126.21, 126.13, TABLE 7-continued 126.07, 126.00, 125.94, 125.88, 125.7, 124.93, 124.88, 117.4, 109.5, 87.4, 87.2, 85.6, 84.5, 83.8, 83.50, 83.46, 82.8, 82.2, 81.8, 81.2, 80.83, 80.77, 80.4, 79.4, 79.22, 79.18, 78.6, 76.8, 75.4, 74.9, 74.0, 73.9, 73.6, 73.51, 73.46, 72.84, 72.81, 72.5, 71.83, 71.75, 71.3, 71.1, 63.3, 62.4, 46.4, 43.3, 42.3, 41.4, 40.7, 40.3, 39.2, 38.5, 37.6, 36.3, 34.9, 34.4, 32.0, 27.7, 27.3, 25.4, 24.2, 22.0, 20.2, 16.4, 14.2, 14.0, 9.8;
MALDI-TOF MS, calcd. for $C_{128}H_{138}NaO_{19}$ 2001.9730 (M + Na$^+$), found for 2001.9711

Synthesis of Compound 8

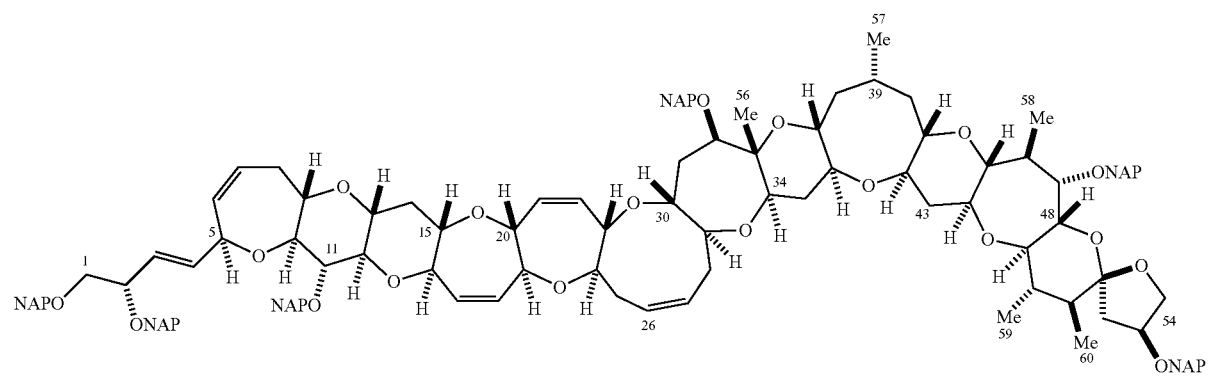

compound 8

(PCy$_3$)$_2$Cl$_2$Ru=CHPh (Grubbs catalyst, 0.2 mg, 0.24 µmol) is added to CH$_2$Cl$_2$ (1.0 mL, 0.7 nM) solution of frozen and de-aired compound 7 (1.3 mg, 0.66 µmol) and stirred at 40° C. for 4 hours. To this solution, Et$_3$N (0.1 mL) is introduced and reaction is stopped, then concentrated and refined by a flush column, thus pentaene (1.0 mg, 0.51 µmol, 78%) of compound 8 is obtained. Features of compound 8 are shown in Table 8.

TABLE 8

[α]$_D^{25}$ −6.2 (c 0.10, CH$_2$Cl$_2$); IR (film) ν 2924, 2854, 1736, 1457, 1268, 1092 cm$^{−1}$;
$^1$H NMR (500 MHz, C$_6$D$_6$) δ 8.00-7.00 (42H, m, NAP × 6), 5.99 (1H, dd, J = 15.5, 3.5 Hz, H4), 5.95 (1H, dd, J = 15.5, 3.5 Hz, H3), 5.89 (1H, d, J = 13.0 Hz, H18), 5.88 (1H, m, H26), 5.88 (1H, m, H27), 5.86 (1H, m H21), 5.78 (1H, d, J = 13.0 Hz, H17), 5.69 (1H, ddd, J = 11.0, 3.0, 3.0 Hz, H6), 5.57 (1H, m, H22), 5.53 (1H, m, H7), 5.26 (2H, s, NAP), 4.99 (1H, d, J = 12.5 Hz, NAP), 4.88 (1H, d, J = 12.5 Hz, NAP), 4.84 (1H, d, J = 12.5 Hz, NAP), 4.83 (1H, d, J = 12.5 Hz, NAP), 4.81 (1H, d, J = 12.5 Hz, NAP), 4.61 (1H, d, J = 12.5 Hz, NAP), 4.55 (1H, m, H5), 4.50 (2H, s, NAP), 4.34 (2H, s, NAP), 4.26 (1H, m, H44), 4.19 (1H, m, H2), 4.10 (1H, m, H54), 4.07 (1H, d, J = 9.5 Hz, H48), 4.01 (1H, d, J = 10.0 Hz, H55), 4.00 (1H, d, J = 9.0 Hz, H20), 3.98 (1H, m, H23), 3.92 (1H, m, H19), 3.84 (1H, d, J = 9.0 Hz, H16), 3.83 (1H, dd, J = 9.5, 9.5 Hz, H49), 3.81 (1H, dd, J = 10.0, 5.0 Hz, H55), 3.74 (1H, dd, J = 9.0, 3.5 Hz, H11), 3.72 (1H, dd, J = 6.5, 6.5 Hz, H30), 3.67 (1H, dd, J = 10.0, 7.0 Hz, H1), 3.67 (1H, d, J = 3.5 Hz, H47), 3.59 (1H, dd, J = 9.0, 9.0 Hz, H10), 3.53 (1H, m, H32), 3.52 (1H, dd, J = 10.0, 4.0 Hz, H1), 3.51 (1H, m, H29), 3.49 (1H, m, H24), 3.46 (1H, m, H37), 3.33 (1H, ddd, J = 9.0, 9.0, 4.0 Hz, H9), 3.27 (1H, dd, J = 9.0, 9.0 Hz, H12), 3.17 (1H, ddd, J = 11.5, 9.0, 4.0 Hz, H15), 3.13 (1H, m, H41), 3.10 (1H, dd, J = 9.0, 4.5 Hz, H45), 3.05 (1H, m, H42), 3.03 (1H, m, H34), 2.96 (1H, m, H13), 2.94 (1H, m, H36), 2.87 (1H, m, H25), 2.86 (1H, m, H28), 2.61 (1H, ddd, J = 16.0, 8.0, 4.0 Hz, H8), 2.58 (1H, m, H25), 2.58 (1H, m, H28), 2.56 (1H, m, H46), 2.48 (1H, ddd, J = 12.0, 5.0, 5.0 Hz, H43), 2.39 (1H, m, H31), 2.34 (1H, m, H14), 2.33 (1H, m, H8), 2.24 (1H, m, H53), 2.23 (1H, m, H53), 2.21 (1H, m, H31), 2.14 (1H, m, H50), 2.09 (1H, m, H40), 2.06 (1H, m, H35), 2.02 (1H, m, H38), 1.87 (1H, m, H39), 1.86 (1H, m, H35), 1.79 (1H, ddd, J = 12.0, 12.0, 12.0 Hz, H43), 1.72 (1H, ddd, J = 11.5, 11.5, 11.5 Hz, H14), 1.66 (1H, m, H40), 1.60 (1H, m, H38), 1.56 (1H, m, H51), 1.36 (3H, s, Me56), 1.29 (3H, d, J = 6.5 Hz, Me59), 1.17 (3H, d, J = 7.5 Hz, Me58), 1.16 (3H, d, J = 7.0 Hz, Me60), 0.98 (3H, d, J = 7.5 Hz, Me57);
MALDI-TOF MS, calcd. for $C_{126}H_{134}NaO_{19}$ 1973.9421 (M + Na$^+$), found for 1973.9417

Synthesis of Aimed Compound CTX1B.

DDQ (1.6 mg, 6.9 μmol) is added to CH$_2$Cl$_2$ (100 μL)-water (100 μL) solution of compound 8 (450 μg, 0.23 μmol) and stirred at room temperature for 45 minutes. Na$_2$S$_2$O$_3$ aqueous solution is added and reaction is stopped, and diluted by ethyl acetate and saturated NaHCO$_3$ aqueous solution. Water phase is extracted by ethyl acetate for 5 times and combined organic layer is washed by saturated brine, then solvent is concentrated. Obtained mixture is refined by HPLC and compound E is obtained. Hydrochloric acid (1N. 50 μL) is added to methanol (200 μL) solution of compound E is added and stirred at room temperature for 30 minutes. Saturated NaHCO$_3$ aqueous solution is added to this solution and reaction is stopped, then concentrated. This mixture is diluted by water and ethyl acetate for 5 times, and combined organic layer is concentrated. Crude CTX1B is refined by HPLC and CTX1B (108 μL mg, 0.097 μmol, 42%) is obtained. Features of synthesized CTX1B are shown in Table 9.

Illustration of Shortened Marks in this Application
AIBN α,α'-azobis(isobutyronitrile)
Cy cyclohexyl
DDQ 2,3-dichloro-5,6-dicyano-1,4-benzoquinone
DIBAL diisobutylaluminumhydride
DMSO dimethylsulfoxide
DTBMP 2,6-di-t-butyl-4-methylpyridine
Grubbs catalyst benzylidene-bis(tricyclohexylphosphine)dichlororuthenium
HPLC high performance liquid chromatography
Me Methanol
NaHMDS sodium bis(trimethylsilyl)amide
NAP 2-naphthylmethyl
Ph phenyl
TBAF tetrabutylammonium fluoride
Tf trifluoromethanesulfonyl

TABLE 9

$^1$H NMR (500 MHz, C$_6$D$_5$N) δ 7.30 (1H, d, J = 4.0 Hz, OH11), 6.75 (1H, d, J = 3.5 Hz, OH47), 6.63 (1H, d, J = 4.0 Hz, OH2), 6.52 (1H, d, J = 4.0 Hz, OH54), 6.39 (1H, t, J = 5.0 Hz, OH1), 6.38 (1H, dd, J = 15..0, 3.0 Hz, H4), 6.35 (1H, dd, J = 15.0, 3.0 Hz, H3), 6.03 (1H, d, J = 13.0 Hz,, H22), 5.97 (1H, m, H26), 5.97 (1H, m, H27), 5.91 (1H, ddd, J = 11.5, 3.0, 3.0 Hz, H6), 5.89 (1H, d, J = 12.5 Hz, H18), 5.53 (1H, dddd, J = 11.5, 8.0, 3.0, 3.0 Hz, H7), 5.74 (1H, d, J = 12.5 Hz, H17), 5.67 (1H, m H21), 5.26 (1H, m, OH54), 4.86 (1H, m, H5), 4.86 (1H, m, H54), 4.69 (1H, m, H2), 4.48 (1H, ddd, J = 12.0, 10.0, 5.0 Hz, H44), 4.22 (1H, dd, J = 3.5, 3.5 Hz, H47), 4.21 (1H, m, H20), 4.19 (1H, m, H55), 4.17 (1H, m, H55), 4.16 (1H, m, H32), 4.10 (1H, ddd, J = 9.0, 9.0, 4.0 Hz, H11), 4.07 (1H, d, J = 10.0 Hz, H48), 4.05 (1H, m, H19), 4.03 (1H, m, H23), 4.02 (1H, d, J = 10.0 Hz, H16), 4.00 (1H, ddd, J = 10.0, 5.0, 5.0 Hz, H1), 3.98 (1H, dd, J = 10.0, 5.0, 5.0 Hz, H1), 3.97 (1H, dd, J = 10.0, 10.0 Hz, H49), 3.78 (1H, m, H29), 3.76 (1H, dd, J = 9.0, 9.0 Hz, H10), 3.61 (1H, m, H24), 3.57 (1H, m, H30), 3.54 (1H, m, H15), 3.50 (1H, m, H37), 3.49 (1H, ddd, J = 9.0, 9.0, 4.0 Hz, H9), 3.44 (1H, dd, J = 9.0, 9.0 Hz, H12), 3.35 (1H, ddd, J = 12.0, 9.0, 4.5 Hz, H13), 3.34 (1H, m, H36), 3.34 (1H, m, H42), 3.32 (1H, dd, J = 12.0, 4.5 Hz, H34), 3.22 (1H, ddd, J = 10.0, 10.0, 3.0 Hz, H41), 3.21 (1H, dd, J = 10.0, 5.0 Hz, H45), 2.94 (1H, m, H25), 2.94 (1H, m, H28), 2.73 (1H, ddd, J = 16.0, 8.0, 4.0 Hz, H8), 2.60 (1H, m, H31), 2.59 (1H, m, H43), 2.59 (1H, m, H46), 2.57 (1H, m, H31), 2.56 (1H, m, H14), 2.53 (1H, m, H8), 2.40 (1H, dd, J = 9.0, 6.5 Hz, H53), 2.36 (1H, m, H28), 2.34 (1H, dd, J = 9.0, 3.5 Hz, H53), 2.26 (1H, ddd, J = 12.0, 4.5, 4.5 Hz, H35), 2.20 (1H, m, H25), 2.04 (1H, m, H40), 2.00 (1H, m, H50), 1.92 (1H, ddd, J = 12.0, 12.0, 12.0 Hz, H35), 1.90 (1H, m, H39), 1.85 (1H, ddd, J = 12.0, 12.0, 12.0 Hz, H14), 1.83 (1H, m, H38), 1.78 (1H, ddd, J = 12.0, 12.0, 12.0 Hz, H43), 1.73 (1H, m, H40), 1.67 (1H, m, H51), 1.54 (1H, m, H38), 1.38 (3H, s, Me56), 1.32 (3H, d, J = 7.0 Hz, Me59), 1.31 (3H, d, J = 6.0 Hz, Me58), 1.23 (3H, d, J = 6.5 Hz, Me60), 0.93 (3H, d, J = 7.0 Hz, Me57);
MALDI-TOF MS, calcd. for C$_{60}$H$_{86}$O$_{19}$ 1133.5661 (M + Na$^+$), found for 1133.5583

THF tetrahydrofuran
TMS trimethylsilyl
TIPS triisopropylsilyl

INDUSTRIAL APPLICABILITY

The present invention makes possible to provide necessary amount of said compound for progressing bioscience research or development of method for detection of ciguatera poisoned fish, and is useful for industrial use applicable as a standard sample for ciguatera food-poisoning happened in all over the world.

The invention claimed is:

1. A method for preparation of CTX1B including the following steps:

[CTX1B structure]

oxidizing the double bond of compound A

[compound A structure]

by osmium tetra oxide to form a diol derivative of compound A, and transforming the diol to aldehyde by oxidative cleavage using sodium periodate, then reducing the aldehyde to alcohol using sodium borohydride and obtaining compound 1;

[compound 1 structure]

transforming the alcohol of compound 1 to compound 2 using diphenyldisulfide·tributylphosphine;

[compound 2 structure]

[compound C structure]

transforming said compound 2 using α-chlorosulphide to synthesize compound B;

[compound B structure]

joining under presence of DTBMP said compound B to ABCDE ring segments of compound C as O,S-acetal using silver triflate and forming compound 3;

compound 3

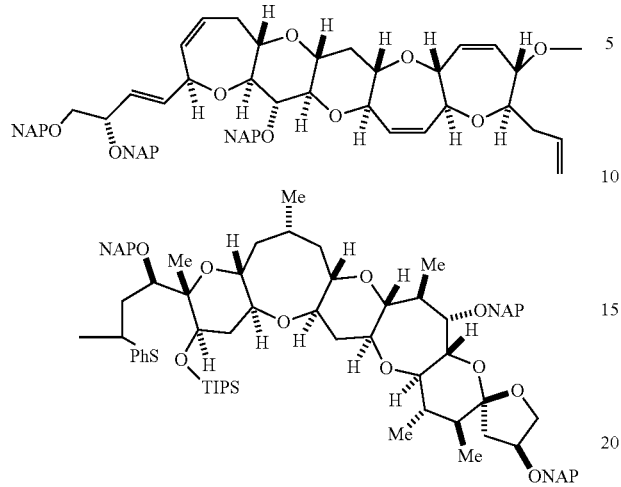

removing TIPS group of said compound 3 using TBAF and forming compound 4;

compound 4

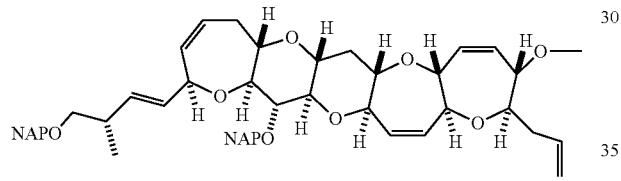

joining pentafluorophenylpropiolate to alcohol of said compound 4 using trimethylphosphine and forming compound 5;

compound 5

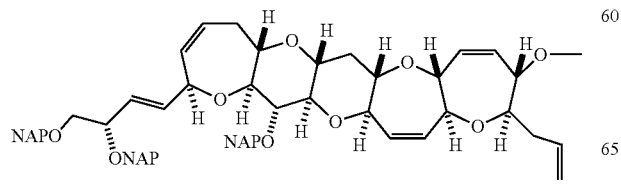

-continued

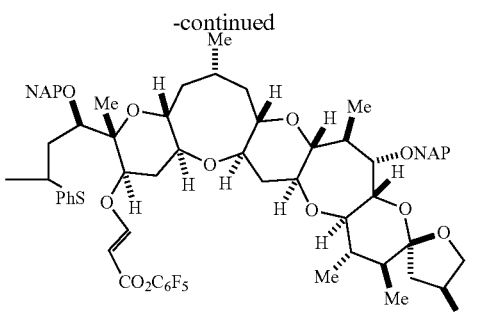

carrying out radical cyclization reaction on said compound 5 by treating with AIBN and tintributyl hydride and forming G ring part, so that said compound 5 transforms to carboxylic acid of compound D;

compound D

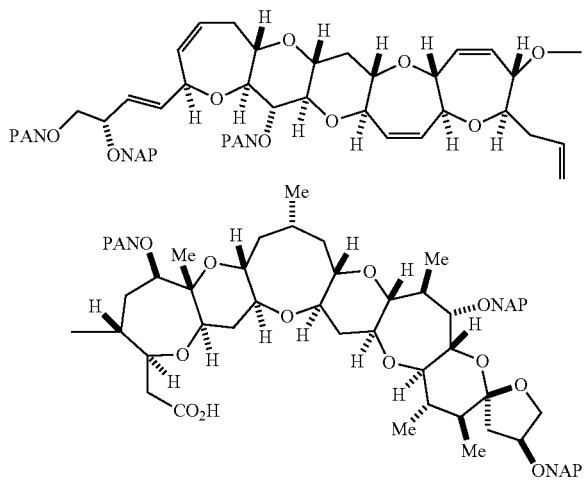

transforming to methyl ester by acting trimethylsilyldiazomethane and forming compound 6;

compound 6

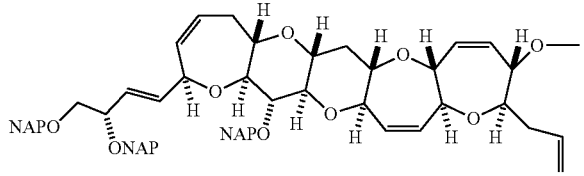

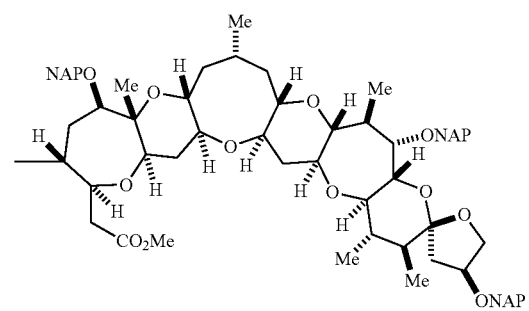

forming compound 7 by reducing methyl ester of said compound 6 by diisobutylaluminum hydrate under lower temperature condition, then transforming to olefin by Wittig reaction;

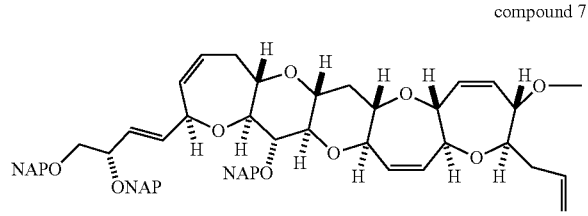

compound 7 forming compound 8 by forming F ring part by carrying out ring closure methathesis reaction using a Grubbs catalyst to said compound 7;

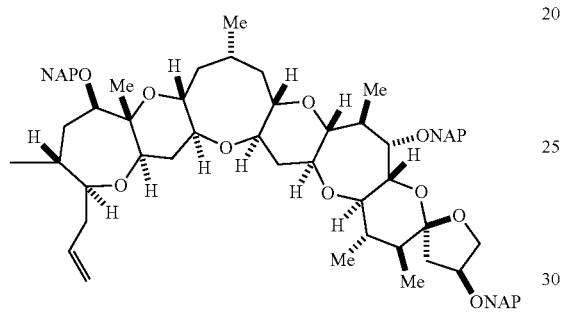

compound 8

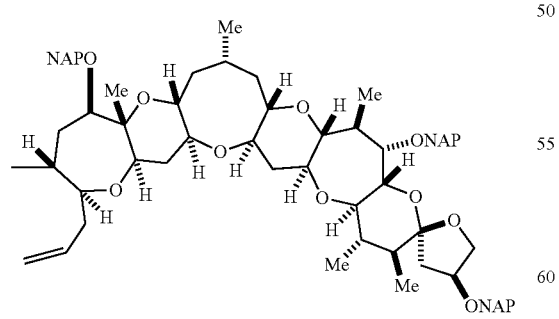

synthesizing compound E, 1,2-diol of A ring side chain of which is protected by naphthylacetal, by oxidizing 6 NAP groups using DDQ and removing 5 NAP groups; and

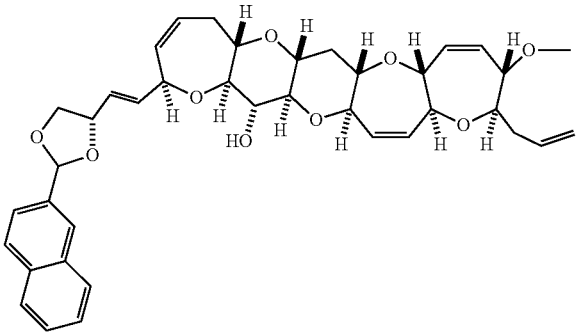

compound E

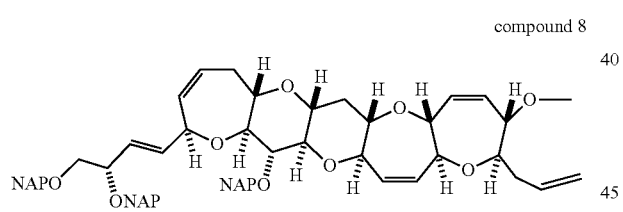

carrying out acid treatment on said compound E and obtaining CTX1B, wherein, in compounds A, B, C, D, E, CTX1B and compounds 1-8, NAP is 2-naphthylmethyl group, Me is methyl group, TIPS is triisopropylsilyl group, Ph is phenyl group, wherein DTBMP is 2,6-di-t-butyl-4-methylpyridine, TBAF is tetrabutylammonium fluoride, AIBN is α, α'-azobis(isobutyronitrile), and DDQ is 2,3-dichloro-5,6-dicyano-1,4-benzoquinone.

2. A novel compound represented by compound 1 to be used for preparation of CTX1B compound 1

3. A novel compound represented by compound 2 to be used for preparation of CTX1B of claim 1 compound 2

4. A novel compound represented by compound 3 to be used for preparation of CTX1B compound 3

5. A novel compound represented by compound 4 to be used for preparation of CTX1B compound 4

6. A novel compound represented by compound 5 to be used for preparation of CTX1B compound 5

7. A novel compound represented by compound 6 to be used for preparation of CTX1B compound 6

8. A novel compound represented by compound 7 to be used for preparation of CTX1B compound 7

9. A novel compound represented by compound 8 to be used for preparation of CTX1B

* * * * *